US00RE36536E

United States Patent [19]

Bronstein

[11] E Patent Number: Re. 36,536

[45] Reissued Date of Patent: Jan. 25, 2000

[54] METHOD OF DETECTING A SUBSTANCE USING ENZYMATICALLY-INDUCED DECOMPOSITION OF DIOXETANES

[75] Inventor: Irena Y. Bronstein, Newton, Mass.

[73] Assignee: Tropix. Inc., Bedford, Mass.

[21] Appl. No.: 08/958,342

[22] Filed: Oct. 27, 1997

Related U.S. Patent Documents

Reissue of:

[64] Patent No.: 4,978,614
Issued: Dec. 18, 1990
Appl. No.: 07/382,125
Filed: Jul. 20, 1989

U.S. Applications:

[

[63] Continuation-in-part of application No. 07/265,406, Oct. 26, 1988, abandoned, which is a continuation-in-part of application No. 06/889,823, Jul. 24, 1986, abandoned.

[51] Int. Cl.[7] ..... G01N 21/76; G01N 33/53

[52] U.S. Cl. ..... 435/21; 435/6; 435/7; 435/18; 435/19; 435/125; 435/810; 536/27

[58] Field of Search ..... 536/27; 435/6, 435/7, 18, 19, 21, 125, 810

[56] References Cited

U.S. PATENT DOCUMENTS

| | | | |
|---|---|---|---|
| 4,857,652 | 8/1989 | Schaap | 549/510 |
| 5,538,847 | 7/1996 | Bronstein et al. | 435/6 |
| 5,639,907 | 6/1997 | Bronstein et al. | 560/13 |
| 5,679,803 | 10/1997 | Bronstein et al. | 549/220 |
| 5,783,361 | 7/1998 | Bronstein et al. | 435/4 |
| 5,840,919 | 11/1998 | Bronstein et al. | 549/22 |
| 5,847,161 | 12/1998 | Bronstein et al. | 549/220 |
| 5,851,771 | 12/1998 | Bronstein et al. | 435/6 |
| 5,869,699 | 2/1999 | Bronstein et al. | 549/219 |

FOREIGN PATENT DOCUMENTS

| | | |
|---|---|---|
| 254051 | 1/1988 | European Pat. Off. . |
| 8800695 | 1/1988 | WIPO . |

OTHER PUBLICATIONS

Zaklika K A et al, J. Amer. Chem Soc. 100:4916, 1978.
Zaklika K A et al, Photochem. Photobiol 30:35, 1979.
Schaap AP, J. Amer. Chem. Soc 104:3504, 1982.
Schaap AP et al, Tet. Litter 23:2943, 1982.
Adam, W et al, Chem. Ber 116:839, 1983.
Meiier, EW et al, J. Chem. Ed. 59:1071, 1982.
Hummelen, JC et al, Meth Enzymol 133:531, 1986.
Schaap, AP et al, Tet Letters 28:1935, 1987.
Schaap, AP et al, Tet. Letters 28:1159, 1987.
Bronstein, I.Y. et al Clin Chem 35:1441, 1989.
Bronstein I.Y. et al Anal. Biochem 180:95, 1989.
Bronstein et al, J. Bioluem Chemilum 4:99, 1989.

*Primary Examiner*—Amelia Owens
*Attorney, Agent, or Firm*—Long Aldridge & Norman LLP; Steven B. Kelber

[57] ABSTRACT

In an assay method in which a member of a specific binding pair is detected by means of an optically detectable reaction, the improvement wherein the optically detectable reaction includes the reaction, with an enzyme, of a dioxetane having the formula where T is a cycloalkyl or polycycloalkyl group bonded to the 4-membered ring portion of the dioxetane by a spiro linkage; Y is a fluorescent chromophore; X is hydrogen, alkyl, aryl, aralkyl, alkaryl, heteroalkyl, heteroaryl, cycloalkyl, cycloheteroalkyl, or enzyme-cleavable group; and Z is hydrogen or an enzyme-cleavable group, provided that at least one of X or Z must be an enzyme-cleavable group, so that the enzyme cleaves the enzyme-cleavable group from the dioxetane to form a negatively charged substituent bonded to the dioxetane, the negatively charged substituent causing the dioxetane to decompose to form a luminescent substance that includes group Y of said dioxetane.

70 Claims, 22 Drawing Sheets top spot = positive control

DETECTION OF ALKALINE PHOSPHATASE USING 0.4 mM AMPPD

AFP ASSAY

COMPARISON OF AMPPD AND PNPP AS SUBSTRATE

TSH ASSAY USING AMPPD AS SUBSTRATE

CEA ASSAY USING AMPPD AS SUBSTRATE

LH ASSAY

QUEST'S hLH ASSAY IMAGED ON POLAROID TYPE 612 FILM pH DEPENDENCE OF B-GALACTOSIDASE ACTIVATED CHEMILUMINESCENCE FROM AMPGD

C T A G

METHOD OF DETECTING A SUBSTANCE USING ENZYMATICALLY-INDUCED DECOMPOSITION OF DIOXETANES

Matter enclosed in heavy brackets [ ] appears in the original patent but forms no part of this reissue specification; matter printed in italics indicates the additions made by reissue.

This application is a continuation-in-part of copending Bronstein U.S. patent application Ser. No. 265,406, filed Oct. 26, 1988, which is a continuation-in-part of copending Bronstein U.S. patent application Ser. No. 889,823 filed July 24, 1986 *both now abandoned*.

FIELD OF THE INVENTION

The invention relates to the use of dioxetanes to detect a substance in a sample.

BACKGROUND OF THE INVENTION

Dioxetanes are compounds having a 4-membered ring in which 2 of the members are adjacent oxygen atoms. Dioxetanes can be thermally or photochemically decomposed to form carbonyl products, e.g., esters, ketones or aldehydes. Release of energy in the form of light (i.e., luminescence) accompanies the decompositions.

SUMMARY OF THE INVENTION

In general, the invention features in a first aspect an improvement in an assay method in which a member of a specific binding pair (i.e., two substances which bind specifically to each other) is detected by means of an optically detectable reaction. The improvement includes the reaction, with an enzyme, a dioxetane having the formula

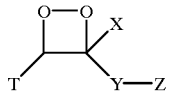

where T is a substituted (i.e., containing one or more $C_1$–$C_7$ alkyl groups or heteroatom groups, e.g., carbonyl groups) or unsubstituted cycloalkyl ring (having between 6 and 12 carbon atoms, inclusive, in the ring) or polycycloalkyl group (having 2 or more fused rings, each ring independently having between 5 and 12 carbon atoms, inclusive), bonded to the 4-membered dioxetane ring by a spiro linkage; Y is a fluorescent chromophore, (i.e., Y is group capable of absorbing energy to form an excited, i.e., higher energy, state, from which it emits light to return to its original energy state); X is hydrogen, a straight or branched chain alkyl group (having between 1 and 7 carbon atoms, inclusive, e.g., methyl), a straight chain or branched heteroalkyl group (having between 1 and 7 carbon atoms, inclusive, e.g., methoxy, hydroxyethyl, or hydroxypropyl), an aryl group (having at least 1 ring, e.g., phenyl), a heteroaryl group (having at least 1 ring, e.g., pyrrolyl or pyrazolyl), a heteroalkyl group (having between 2 and 7 carbon atoms, inclusive, in the ring, e.g., dioxane), an aralkyl group (having at least 1 ring, e.g., benzyl), an alkaryl group (having at least 1 ring, e.g., tolyl), or an enzyme-cleavable group, i.e., a group having a bond which can be cleaved by an enzyme to yield an electron-rich moiety bonded to the dioxetane, e.g., phosphate, where a phosphorus-oxygen bond can be cleaved by an enzyme, e.g., acid phosphatase or alkaline phosphatase, to yield a negatively charged oxygen bonded to the dioxetane; and Z is hydrogen, hydroxyl, or an enzyme-cleavable group (as defined above), 10 provided that at least one of X or Z must be an enzyme-cleavable group, so that the enzyme cleaves the enzyme-cleavable group to form a negatively charged substituent (e.g., an oxygen anion) bonded to the dioxetane, the negatively charged substituent causing the dioxetane to decompose to form a luminescent substance (i.e., a substance that emits energy in the form of light) that includes group Y. The luminescent substance is detected as an indication of the presence of the first substance. By measuring the intensity of luminescence, the concentration of the first substance can be determined.

In preferred embodiments, one or more of groups T, X, or Y further include a solubilizing substituent, e.g., carboxylic acid, sulfonic acid, or quaternary amino salt; group T of the dioxetane is a polycycloalkyl group, preferably adamantyl; the enzyme-cleavable group includes phosphate; and the enzyme includes phosphatase.

The invention also features a kit for detecting a first substance in a sample.

In a second aspect, the invention features a method of detecting an enzyme in a sample. The method involves contacting the sample with the above-described dioxetane in which group Z is capable of being cleaved by the enzyme being detected. The enzyme cleaves group Z to form a negatively charged substituent (e.g., an oxygen anion) bonded to the dioxetane. This substituent destabilizes the dioxetane, thereby causing the dioxetane to decompose to form a luminescent substance that includes group Y of the dioxetane. The luminescent substance is detected as an indication of the presence of the enzyme. By measuring the intensity of luminescence, the concentration of the enzyme can also be determined.

The invention provides a simple, very sensitive method for detecting substances in samples, e.g., biological samples, and is particularly useful for substances present in low concentrations. Because dioxetane decomposition serves as the excitation energy source for chromophore Y, an external excitation energy source, e.g., light, is not necessary. In addition, because the dioxetane molecules are already in the proper oxidation state for decomposition, it is not necessary to add external oxidants, e.g., $H_2O_2$ or $O_2$. Enzyme-activated decomposition allows for high sensitivity because one enzyme molecule can cause many dioxetane molecules to luminesce, thus creating an amplification effect. Moreover, the wavelength (or energy) of emission and the quantum yields of luminescence can be varied according to the choice of the Y substituent of the dioxetane (as used herein, "quantum yield" refers to the number of photons emitted from the luminescent product per number of moles of dioxetane decomposed). In addition, through appropriate modifications of the T, X, and Y groups of the dioxetane, the solubility of the dioxetane and the kinetics of dioxetane decomposition can be varied. The dioxetanes can also be attached to a variety of molecules, e.g., proteins or haptens, or immobilization substrates, e.g., polymer membranes, or included as a side group in a homopolymer or copolymer.

Other features and advantages of the invention will be apparent from the following description of the preferred embodiments thereof, and from the claims.

DESCRIPTION OF THE PREFERRED EMBODIMENTS

Figure 1:
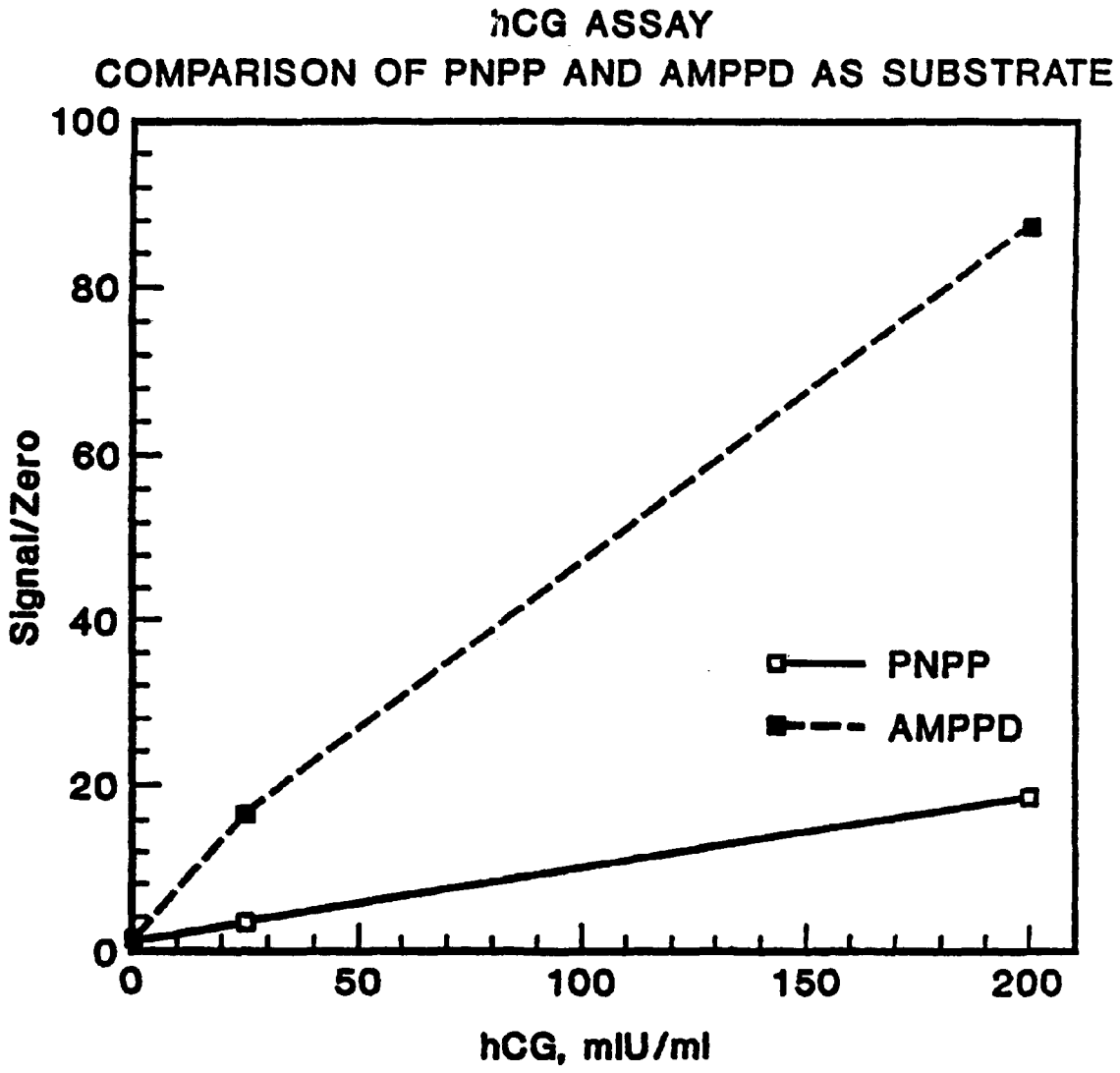
FIG. 1 compares a solid state quantitative colorimetric assay for human chorionic gonadotropin (hCG) using p-nitrophenyl phosphate (PNPP) as chromogen with the quantitative chemiluminescence assay of the invention using 3-(2'-spiroadamantane)-4-methoxy-4-(3"-phosphoryloxy) phenyl-1,2-dioxetane, disodium salt (AMPPD) as the lumogen.

The structure, synthesis, and use of preferred embodiments of the invention will now be described.

Structure

The invention employs dioxetanes having the structure recited in the Summary of the Invention above. The purpose of group T is to stabilize the dioxetane, i.e., to prevent the dioxetane from decomposing before the enzyme-cleavable group Z is cleaved. Large, bulky, sterically hindered molecules, e.g., fused polycyclic molecules, are the most effective stabilizers. In addition, T preferably contains only C—C and C—H single bonds. The most preferred molecule is an adamantyl group consisting of 3 fused cyclohexyl rings. The adamantyl group is bonded to the 4-membered ring portion of the dioxetane through a spiro linkage.

Group Y is a fluorescent chromophore bonded to enzyme-cleavable group Z. Y becomes luminescent when an enzyme cleaves group Z, thereby creating an electron-rich moiety which destabilizes the dioxetane, causing the dioxetane to decompose. Decomposition produces two individual carbonyl compounds, one of which contains group T, and the other of which contains groups X, Y, and Z; the energy released from dioxetane decomposition causes the Y groups of the latter carbonyl compound to luminesce (if group X is hydrogen, an aldehyde is produced).

The excited state energy of chromophore Y (i.e., the energy chromophore Y must possess in order to emit light) is preferably less than the excited state energy of the ketone containing group T in order to confine luminescence to group Y. For example, when Y is adamantyl, the excited state energy of chromophore Y is preferably less than the excited state energy of spiroadamantane.

Any chromophore Y can be used according to the invention. In general, it is desirable to use a chromophore which maximizes the quantum yield in order to increase sensitivity.

Examples of suitable chromophores include the following:

(1) anthracene and anthracene derivatives, e.g., 9,10-diphenylanthracene, 9-methylanthracene, 9-anthracene carboxaldehyde, anthryl alcohols and 9-phenylanthracene;

(2) rhodamine and rhodamine derivatives, e.g., rhodols, tetramethyl rhodamine, tetraethyl rhodamine, diphenyldimethyl rhodamine, diphenyldiethyl rhodamine, and dinaphthyl rhodamine;

(3) fluorescein and fluorescein derivatives, e.g., 5-iodoacetamido fluorescein. 6-iodoacetamido fluorescein, and fluorescein-5-maleimide;

(4) eosin and eosin derivatives, e.g., hydroxy eosins, eosin-5-iodoacetamide, and eosin-5-maleimide;

(5) coumarin and coumarin derivatives, e.g., 7-dialkylamino-4-methylcoumarin, 4-bromomethyl-7-methoxycoumarin, and 4-bromomethyl-7-hydroxycoumarin;

(6) erythrosin and erythrosin derivatives, e.g., hydroxy erythrosins, erythrosin-5-iodoacetamide and erythrosin-5-maleimide;

(7) aciridine and aciridine derivatives, e.g., hydroxy aciridines and 9-methyl aciridine;

(8) pyrene and pyrene derivatives, e.g., N-(1-pyrene) iodoacetamide, hydroxy pyrenes, and 1-pyrenemethyl iodoacetate;

(9) stilbene and stilbene derivatives, e.g., 6,6'-dibromostilbene and hydroxy stilbenes;

(10) naphthalene and naphthalene derivatives, e.g., 5-dimethylaminonaphthalene-1-sulfonic acid and hydroxy naphthalene;

(11) nitrobenzoxadiazoles and nitrobenzoxadiazole derivatives, e.g., hydroxy nitrobenzoxadiazoles, 4-chloro-7-nitrobenz-2-oxa-1,3-diazole, 2-(7-nitrobenz-2-oxa-1,3-diazol-4-yl-amino)hexanoic acid;

(12) quinoline and quinoline derivatives, e.g., 6-hydroxyquinoline and 6.aminoquinoline;

(13) acridine and acridine derivatives, e.g., N-methylacridine and N-phenylacridine;

(14) acidoacridine and acidoacridine derivatives, e.g., 9-methylacidoacridine and hydroxy-9-methylacidoacridine;

(15) carbazole and carbazole derivatives, e.g., N-methylcarbazole and hydroxy-N-methylcarbazole;

(16) fluorescent cyanines, e.g., DCM (a laser dye), hydroxy cyanines, 1,6-diphenyl-1,3,5-hexatriene, 1-(4-dimethyl aminophenyl)-6-phenylhexatriene, and the corresponding 1,3-butadienes.

(17) carbocyanine and carbocyanine derivatives, e.g., phenylcarbocyanine and hydroxy carbocyanines;

(18) pyridinium salts, e.g., 4(4-dialkyldiaminostyryl) N-methyl pyridinium iodate and hydroxy-substituted pyridinium salts;

(19) oxonols; and

(20) resorofins and hydroxy resorofins.

The most preferred chromophores are hydroxy derivatives of anthracene or naphthalene; the hydroxy group facilitates bonding to group Z.

Group Z is bonded to chromophore Y through an enzyme-cleavable bond. Contact with the appropriate enzyme cleaves the enzyme-cleavable bond, yielding an electron-rich moiety bonded to a chromophore Y; this moiety initiates the decomposition of the dioxetane into two individual carbonyl compounds e.g., into a ketone or an ester and an aldehyde if group X is hyrdogen. Examples of electron-rich moieties include oxygen, sulfur, and amine or amino anions. The most preferred moiety is an oxygen anion. Examples of suitable Z groups, and the enzymes specific to these groups are given below in Table 1; an arrow denotes the enzyme-cleavable bond. The most preferred group is a phosphate ester, which is cleaved by alkaline or acid phosphatase enzymes.

TABLE 1

| Group Z | Enzyme |
|---|---|
| (1) 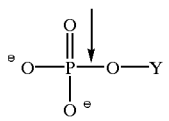 phosphate ester | alkaline and acid phosphatases |
| (2) 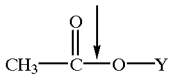 acetate ester | esterases |
| (3) 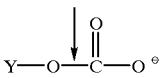 carboxyl | decarboxylases |
| (4) 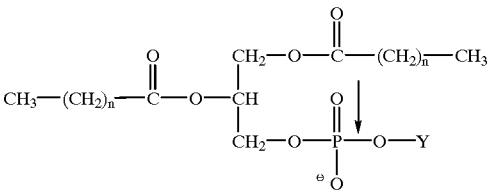 3-phospho-1,2-diacyl glycerides | phospholipase D |

TABLE 1-continued
| Group Z | Enzyme |
|---|---|
| (5) 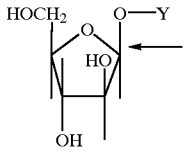  β-D-xyloside | β-xylosidase |
| (6) 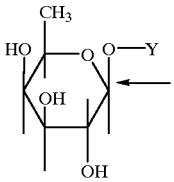  β-D-fucoside | β-D-fucosidase |
| (7) 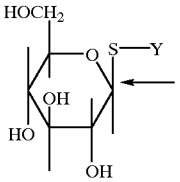  1-thio-D-glucoside | thioglucosidase |
| (8) 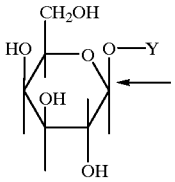  β-D-galactoside | β-D-galactosidase |
| (9) 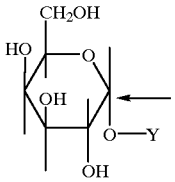  α-D-galactoside | α-D-galactosidase |
| (10) 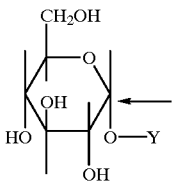  α-D-glucoside | α-D-glucosidase |

TABLE 1-continued
| Group Z | Enzyme |
|---|---|
| (11) 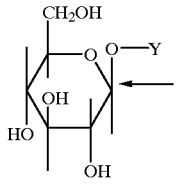 β-D-glucoside | β-D-glucosidase |
| (12) 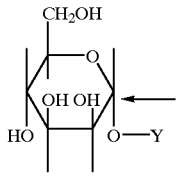 α-D-mannoside | α-D-mannosidase |
| (13) 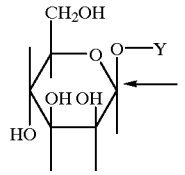 β-D-mannoside | β-D-mannosidase |
| (14) 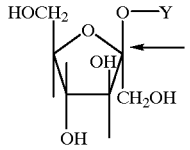 β-D-fructofuranoside | β-D-fructofuranosidase |
| (15) 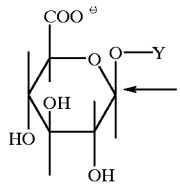 β-D-glucosiduronate | β-D-glucosiduronase |
| (16) 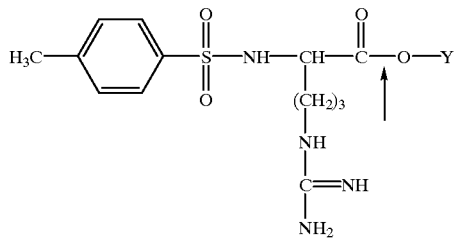 p-toluenesulfonyl-L-arginine ester | trypsin |

TABLE 1-continued

| Group Z | Enzyme |
|---|---|
| (17) 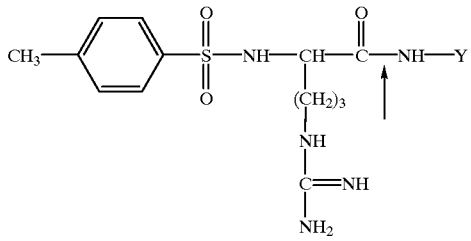 p-toluenesulfonyl-L-arginine amide | trypsin |

Suitable X groups are described in the Summary of the Invention, above. Preferably, X contains one or more solubilizing substituents, i.e., substituents which enhance the solubility of the dioxetane in aqueous solution Examples of solubilizing substituents include carboxylic acids, e.g., acetic acid; sulfonic acids, e.g., methanesulfonic acid; and quaternary amino salts, e.g., ammonium bromide; the most preferred solubilizing substituent is methane-or ethanesulfonic acid.

Preferably, the enzyme which cleaves group Z is covalently bonded to a substance having a specific affinity for the substance being detected. Examples of specific affinity substances include antibodies, e.g., anti-hCG; antigens, e.g., hCG, where the substance being detected is an antibody, e.g., anti-hCG; a probe capable of binding to all or a portion of a nucleic acid, e.g., DNA or RNA, being detected; or an enzyme capable of cleaving the Y—Z bond. Bonding is preferably through an amide bond.

Synthesis

In general, the dioxetanes of the invention are synthesized in two steps. The first step involves synthesizing an appropriately substituted olefin having the formula

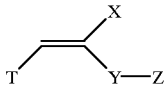

wherein T, X, Y, and Z are as described above. These olefins are preferably synthesized using the Wittig reaction, in which a ketone containing the T group is reacted with a phosphorus ylide (preferably based on triphenylphosphine) containing the X, Y, and Z groups, as follows:

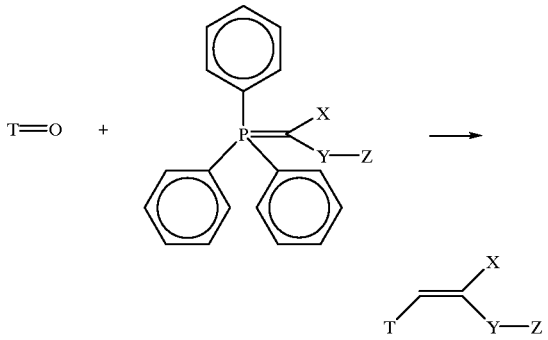

The reaction is preferably carried out below about −70° C. in an ethereal solvent, e.g., tetrahydrofuran (THF).

The phosphorus ylide is prepared by reacting triphenyl phosphine with a halogenated compound containing the X, Y, and Z groups in the presence of base; examples of preferred bases include n-butyllithium, sodium amide, sodium hydride, and sodium alkoxide; the most preferred base is n-butyllithium. The reaction sequence is as follows:

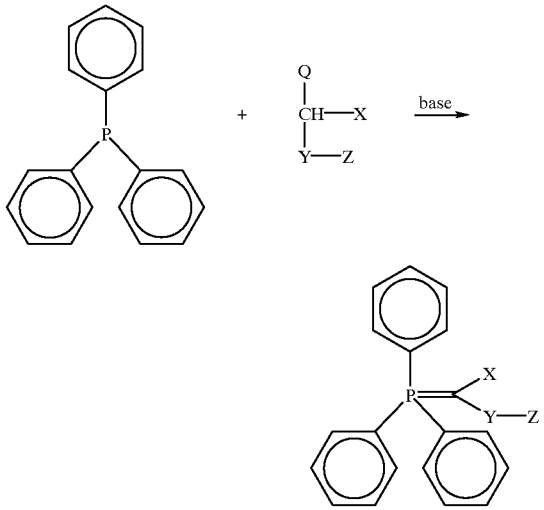

where Q is a halogen, e.g., Cl, Br, or I. The preferred halogen is Br. The reaction is preferably carried out below about −70° C. in THF.

The olefin where T is adamantyl (Ad), X is methoxy ($OCH_1$), Y is anthracene (An), and Z is phosphate ($PO_4$) can be synthesized as follows.

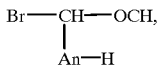

is phosphorylated by treating it with the product of phosphorus acid reacted in the presence of $HgCl_2$ with N-methylimidazole; the net result is to replace the hydroxyl group of An with a phosphate group. The phosphorylated product is then reacted with triphenylphospine below about −70° C. in THF to form the phosphorus ylide having the formula

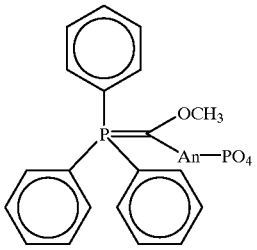

The reaction is conducted in a dry argon atmosphere, Spiroadamantanone (Ad=O) is then added to the solution containing the ylide, while maintaining the temperature below about −70° C., to form the olefin having the formula

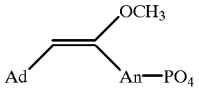

The olefin is then purified using conventional chromatography methods.

The second step in the synthesis of the dioxetanes involves converting the olefin described above to the dioxetane. Preferably, the conversion is effected photochemically by treating by olefin with singlet oxygen ($^1O_2$) in the presence of light. $^1O_2$ adds across the double bond to form the dioxetane as follows:

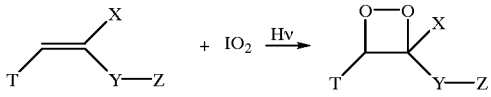

The reaction is preferably carried out below about −70° C. in a halogenated solvent, e.g., methylene chloride. $^1O_2$ is generated 10 using a photosensitizer. Examples of photosensitizers include polymer-bound Rose Bengal (commercially known as Sensitox I and available from Hydron Laboratories, New Brunswick, N.J.), which is preferred, and methylene blue (a well-known dye and pH indicator).

The synthesis of the dioxetane having the formula

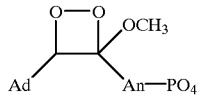

follows.

The olefin having the formula

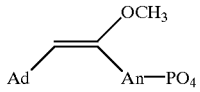

is dissolved in methylene chloride, and the solution is placed in a 2-$cm^2$ pyrex tube equipped with a glass paddle; the paddle is driven from above by an attached, glass enclosed, bar magnet. The solution is cooled to below about −70° C. and 1 g of polymer-bound Rose Bengal is added with stirring. Oxygen is then passed over the surface of the agitated solution while the reaction tube is exposed to light from a 500 W tungsten-halogen lamp (GE Q500 Cl) equipped with a UV-cut off filter (Corning 3060: transmission at 365 nm=0.5%). Thin layer chromatography (tlc) is used to monitor the disappearance of the olefin and the concurrent appearance of the dioxetane. After the reaction is complete (as indicated by tlc), the solvent is removed and the dioxetane is isolated.

Use

A wide variety of assays exist which use visually detectable means to determine the presence or concentration of a particular substance in a sample. The above-described dioxetanes can be used in any of these assays. Examples of such assays include immunoassays to detect antibodies or antigens, e.g., α or β-hCG; enzyme assays; chemical assays to detect, e.g., potassium or sodium ions; and nucleic acid assays to detect, e.g., viruses (e.g., HTLV III or cytomegalovirus, or bacteria (e.g., E. coli)).

When the detectable substance is an antibody, antigen, or nucleic acid, the enzyme capable of cleaving group Z of the dioxetane is preferably bonded to a substance having a specific affinity for the detectable substance (i.e., a substance that binds specifically to the detectable substance), e.g, an antigen, antibody, or nucleic acid probe, respectively. Conventional methods, e.g., carbodiimide coupling, are used to bond the enzyme to the specific affinity substance; bonding is preferably through an amide linkage.

In general, assays are performed as follows. A sample suspected of containing a detectable substance is contacted with a buffered solution containing an enzyme bonded to a substance having a specific affinity for the detectable substance. The resulting solution is incubated to allow the detectable substance to bind to the specific affinity portion of the specific affinity-enzyme compound. Excess specific affinity-enzyme compound is then washed away, and a dioxetane having a group Z that is cleavable by the enzyme portion of the specific affinity-enzyme compound is added. The enzyme cleaves group Z, causing the dioxetane to decompose into two carbonyl compounds (e.g., an ester or ketone when group X is other than hydrogen and an aldehyde when group X is hydrogen); chromophore Y bonded to one of the ketones is thus excited and luminesces. Luminescence is detected using e.g., a cuvette or camera luminometer, as an indication of the presence of the detectable substance in the sample. Luminescence intensity is measured to determine the concentration of the substance.

When the detectable substance is an enzyme, a specific affinity substance is not necessary. Instead, a dioxetane having a Z group that is cleavable by the enzyme being detected is used. Therefore, an assay for the enzyme involves adding the dioxetane to the enzyme-containing sample, and detecting the resulting luminescence as an indication of the presence and the concentration of the enzyme.

Examples of specific assays follow.

A. Assay for Human IgG

A 96-well microtiter plate is coated with sheep anti-human IgG ($F(ab)_2$ fragment specific). A serum sample containing human IgG is then added to the wells, and the wells are incubated for 1 hour at room temperature.

Following the incubation period, the serum sample is removed from the wells, and the wells are washed four times with an aqueous buffer solution containing 0.15 M NaCl, 0.01 M phosphate, and 0.1% bovine serum albumin (pH 7.4).

Alkaline phosphatase bonded to anti-human IgG is added to each well, and the wells are incubated for 1 hr. The wells are then washed four times with the above buffer solution, and a buffer solution of a phosphate-containing dioxetane is added. The resulting luminescence caused by enzymatic degradation of the dioxetane is detected in a luminometer, or with photographic film in a camera luminometer.

B. Assay for hCG

Rabbit anti-α-hCG is adsorbed onto a nylon-mesh membrane. A sample solution containing hCG, e.g., urine from a pregnant woman, is blotted through the membrane, after which the membrane is washed with 1 ml of a buffer solution containing 0.15 M NaCl, 0.01 M phosphate, and 0.1% bovine serum albumin (pH 7.4).

Alkaline phosphatase-labelled anti-β-hCG is added to the membrane, and the membrane is washed again with 2 ml of the above buffer solution. The membrane is then placed in the cuvette of a luminometer or into a camera luminometer, and contacted with a phosphate-containing dioxetane. The luminescence resulting from enzymatic degradation of the dioxetane is then detected.

C. Assay for Serum Alkaline Phosphatase 2.7 ml of an aqueous buffer solution containing 0.8 M 2-methyl-2-aminopropanol is placed in a 12×75 mm pyrex test tube, and 0.1 ml of a serum sample containing alkaline phosphatase added. The solution is then equilibrated to 30° C. 0.2 ml of a phosphate-containing dioxetane is added, and the test tube immediately placed in a luminometer to record the resulting luminescence. The level of light emission will be proportional to the rate of alkaline phosphatase activity.

D. Nucleic Acid Hybridization Assay

A sample of cerebrospinal fluid (CSF) suspected of containing cytomegalovirus is collected and placed on a nitrocellulose membrane. The sample is then chemically treated with urea or guanidinium isothiocyanate to break the cell walls and to degrade all cellular components except the viral DNA. The strands of the viral DNA thus produced are separated and attached to the nitrocellulose filter. A DNA probe specific to the viral DNA and labelled with alkaline phosphatase is then applied to the filter; the probe hybridizes with the complementary viral DNA strands. After hybridization, the filter is washed with an aqueous buffer solution containing 0.2 M NaCl and 0.1 mM Tris-HCl (pH=8.10) to remove excess probe molecules. A phosphate-containing dioxetane is added and the resulting luminescence from the enzymatic degradation of the dioxetane is measured in a luminometer or detected with photographic film.

E. Assay for Galactosidase

In the assays described above and in the Examples to follow dioxetanes containing α- or β- galactosidase-cleavable α-D- or β-D-galactopyranoside groups, respectively, can be added, and the luminescence resulting from the enzymatic cleavage of the sugar moiety from the chromophore measured in a luminometer or detected with photographic film.

F. Electrophoresis

Electrophoresis allows one to separate complex mixtures of proteins and nucleic acids according to their molecular size and structure on gel supports in an electrical field. This technique is also applicable to separate fragments of protein after proteolysis, or fragments of nucleic acids after scission by restriction endonucleases (as in DNA sequencing). After electrophoretic resolution of species in the gel, or after transfer of the separated species from a gel to a membrane, the bonds are probed with an enzyme bound to a ligand. For example, peptide fragments are probed with an antibody covalently linked to alkaline phosphatase. For another example, in DNA sequencing alkaline phosphatase—avidin binds to a biotinylated nucleotide base. Thereafter, AMPPD is added to the gel or membrane filter. After short incubation, light is emitted as the result of enzymatic activation of the dioxetane to form the emitting species. The luminescence is detected by either X-ray or instant photographic film, or scanned by a luminometer. Multichannel analysis further improves the process by allowing one to probe for more than one fragment simultaneously. G. In solid state assays, it is desireable to block nonspecific binding to the matrix by pretreatment of nonspecific binding sites with nonspecific proteins such as bovine serum albumin (BSA) or gelatin. Applicant has determined that some commercial preparations of BSA contain small amounts of phosphatase activity that will produce undesirable background chemiluminescence from AMPPD. Applicant has discovered that certain water-soluble synthetic macromolecular substances are efficient blockers of nonspecific binding in solid state assays using dioxetanes. Preferred among such substances are water-soluble polymeric quaternary ammonium salts such as poly(vinylbenzyltrimethyl-ammonium chloride) (TMQ) or poly[vinylbenzyl(benzyldimethyl-ammonium chloride)] (BDMQ).

H. Assay for Nucleotidase

An assay for the enzyme ATPase is performed in two steps. In the first step, the enzyme is reacted at its optimal pH (typically pH 7.4) with a substrate comprising ATP covalently linked via a terminal phosphoester bond to a chromophore-substituted 1,2-dioxetane to produce a phosphoryl-chromophore-substituted 1,2-dioxetane. In the second step, the product of the first step is decomposed by the addition of acid to bring the pH to below 6, preferably to pH 2–4, and the resulting light measured in a luminometer or detected with chromatographic film. In a similar two-step procedure, ADPase is assayed using as the substrate an ADP derivative of a chromophore-substituted 1,2-dioxetane, and 5'-nucleotidase assayed using as the substrate an adenylic acid derivative of a chromophore-substituted 1,2-dioxetane. The second step can also be carried out by adding the enzyme alkaline phosphatase to decompose the phosphoryl-chromophore-substituted 1,2-dioxetane.

I. Nucleic Acid Sequencing

DNA or RNA fragments, produced in sequencing protocols, can be detected after electrophoretic separation using the chemiluminescent 1,2-dioxetanes of this invention.

DNA sequencing can be performed by a dideoxy chain termination method [Sanger, F., et al., Proc. Nat. Acad. Sci. (USA). 74:5463 (1977)]. Briefly, for each of the four sequencing reactions, single-stranded template DNA is mixed with dideoxynucleotides and biotinylated primer strand DNA. After annealing, Klenow enzyme ant deoxyadenosine triphosphate are incubated with each of the four sequencing reaction mixtures, then chase deoxynucleotide triphosphate is added and the incubation continued.

Subsequently, DNA fragments in reaction mixtures are separated by polyacrylamide gel electrophoresis (PAGE). The fragments are transferred to a membrane, preferably a nylon membrane, and the fragments cross-linked to the membrane by exposure to UV light, preferably of short wave length.

After blocking non-specific binding sites with a polymer, e.g., heparin, casein or serum albumin, the DNA fragments on the membrane are contacted with avidin or streptavidin covalently linked to an enzyme specific for the enzyme-cleavable group of the 1,2-dioxetane substrates of this invention. As avidin or streptavidin bind avidly to biotin, biotinylated DNA fragments will now be tagged with an enzyme. For example when the chemiluminescent substrate is 3-(2'-spiroadamantane)-4-methoxy-4-(3"-phosphoryloxy) phenyl-1,2-dioxetane salt (AMPPD), avidin or streptavidin will be conjugated to a phosphatase. Similarly, when the chemiluminescent substrate is 3-(2'-spiroadamantane)-4-methoxy-4-(3"-β-D-galactopyranosyl)phenyl-1,2-dioxetane (AMPGD), avidin or streptavidin are conjugated with β-galactosidase.

Following generation of luminescence by contacting the complex of DNA fragment-biotin-avidin (or streptavidin)-enzyme with the appropriate 1,2-dioxetane at alkaline pH values, e.g., above about pH 8.5, DNA fragments are visualized on lightsensitive film, e.g, X-ray or instant film, or in a photoelectric luminometer instrument.

The detection method outlined above can also be applied to the genomic DNA sequencing protocol of Church et al. [Church, G.M., et al., Proc. Nat. Acad. Sci. (USA), 81:1991 (1984)]. After transferring chemically cleaved and electrophoretically separated DNA [Maxam, A.M. et al., Proc. Nat. Acad. Sci. (USA), 74:560 (1977)] to a membrane, preferably a nylon membrane, and cross-linking the ladders to the membrane by UV light, specific DNA sequences may be detected by sequential addition of: biotinylated oligonucleotides as hybridization probes; avidin or streptavidin covalently linked to an enzyme specific for an enzyme-cleavable chemiluminescent 1,2-dioxetane of this invention; and, the appropriate 1,2-dioxetane. Images of sequence ladders (produced by PAGE) may be obtained as described above.

Serial reprobing of sequence ladders can be accomplished by first stripping the hybridized probe and chemiluminescent material from a membrane by contacting the membrane with a heated solution of a detergent, e.g., from about 0.5 to about 5% sodium dodecylsulfate (SDS) in water at from about 80° C. to about 90° C., cooling to from about 50° C. to about 70° C., hybridizing the now-naked DNA fragments with another biotinylated oligonucleotide probe to generate a different sequence, then generating an imaging chemiluminescence as described above.

Similar visualization methods can be applied to RNA fragments generated by RNA sequencing methods.

Other embodiments are within the following claims.

For example, the enzyme-cleavable group Z can be bonded to group X of the dioxetane, instead of group Y. The specific affinity substance can be bonded to the dioxetane through groups X, Y, or T (preferably group X), instead of the enzyme. In this case, the group to which the specific affinity substance is bonded is provided with, e.g., a carboxylic acid, amino, or maleimide substituent to facilitate bonding.

Groups X, Y, or T of the dioxetane can be bonded to a polymerizable group, e.g., a vinyl group, which can be polymerized to form a homopolymer or copolymer.

Groups X, Y, or T of the dioxetane can be bonded to, e.g., membranes, films, beads, or polymers for use in immuno- or nucleic acid assays. The groups are provided with, e.g., carboxylic acid, amino, or maleimide substituents to facilitate bonding.

Groups X, Y, or T of the dioxetane can contain substituents which enhance the kinetics of the dioxetane enzymatic degradation, e.g., electron-rich moieties (e.g., methoxy).

Groups Y and T of the dioxetane, as well as group X, can contain solubilizing substituents.

Appropriately substituted dioxetanes can be synthesized chemically, as well as photochemically. For example, the olefin prepared from the Wittig reaction can be epoxidized using a peracid, e.g., p-nitroperbenzoic acid. The epoxidized olefin can then be converted to the dioxetane by treatment with an ammonium salt, e.g., tetramethylammonium hydroxide.

Another example of a chemical synthesis involves converting the olefin prepared from the Wittig reaction to a 1,2-hydroperoxide by reacting the olefin with $H_2O_2$ and dibromantin (1,3-dibromo-5,5-dimethyl hydantoin). Treatment of the 1,2-bromohydroperoxide with base, e.g., an alkali or alkaline earth methalhydroxide such as sodium hydroxide or a silver salt, e.g., silver bromide, forms the dioxetane.

Olefin precursors for the dioxetane can be synthesized by reacting a ketone with a ester in the presence of TiCl and lithium aluminum hydride (LAH). For example, to synthesize an olefin where T is adamantyl (Ad), X is methoxy ($OCH_3$), Y is anthracene (An), and Z is phosphate ($PO_4$), the following reaction sequence is used:

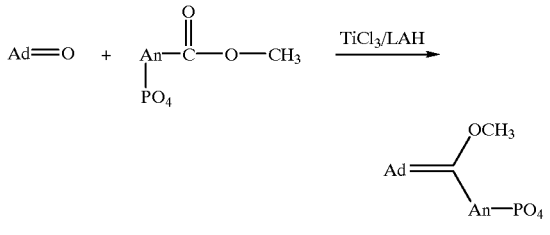

To phosphorylate chromophore Y, e.g., anthracene, a hydroxyl derivative of the chromophore, e.g., hydroxy anthracene, can be reacted with a cyclic acyl phosphate having the following formula:

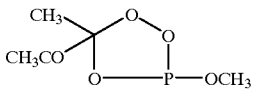

The reaction product is then hydrolyzed with water to yield the phosphorylated chromophore. The cyclic acyl phosphate is prepared by reacting 2,2,2-trimethoxy-4,5-dimethyl-1,3-dioxaphospholene with phosgene at 0° C., following by heating at 120° C. for 2 hr.

The following examples are intended to illustrate the invention in detail, but they are in no way to be taken as limiting, and the present invention is intended to encompass modifications and variations of these examples within the framework of their contents and the claims.

EXAMPLE 1

Bead Format Human Chorionic Gonadotrophin (hCG) Assay, (Serum or Urine)

In the following, an hCG assay method is described in which 3-(2'spiroadamantane)-4-methoxy-4-(3"-phosphoryloxy)phenyl-1,2 dioxetane, disodium salt (AMPPD, synthesized as described above), was used as a substrate of aIkaline phosphatase. For comparison, a colorimetric assay was conducted using p-nitrophenylphosphoric acid (PNPP) as a substrate.

1. Placed one bead which was previously coated with anti-hCG in each tube (12×75 mm) after blotting excess buffer from bead.
2. Added 100 μl of anti-hCG antibody-alkaline phosphatase conjugate to each tube.
3. To each tube added 100 μof sample. Separate tubes were prepared for each of the following:
   (a) Control Zero Sample, (male serum or urine)
   (b) 25 mIU/ml hCG standard (serum or urine)
   (c) 200 mIU/ml hCG standard (serum or urine)
   (d) Patient sample (serum or urine)
4. After mixing, the tubes were covered and incubated for 90 minutes at 37° C.
5. The reaction solution containing the conjugate and sample were aspirated to waste.
6. The beads were washed 3 times with 2.0 ml of phosphate buffered saline, pH 7.4, containing 0.1% Tween 20.

| For Colorimetric Assay | Chemiluminescence |
|---|---|
| 7. N/A | 7. Washed once with 0.05 M carbonate, 1 mM $MgCl_2$ pH 9.5. |
| 8. Added 200 μl 1 mg/ml p-nitrophenyl-phosphate (PNPP) in 0.1 M glycine, 1 mM $MgCl_2$, pH 10.4 | 8. Added 250 μl of 0.4 mM AMPPD in 0.05 M carbonate, 1 mM $MgCl_2$, pH 9.5 |
| 9. Incubated for 30 minutes at room temperature | 9. Incubated for 20 minutes at 30° C. |
| 10. Added 11.5 ml of 0.1 M glycine, 10 mM of EDTA, pH 9.5, to stop color development | 10. N/A |
| 11. Read absorbance at 405 nm in spectrophotometer | 11. Read 10 sec. integral of luminescence from each tube in Turner 20E Luminometer |

12. Plotted both sets of data as the signal at each concentration of hCG divided by the signal at zero hCG vs. concentration of hCG. Typical data are plotted in FIG. 1, wherein PNPP represents the colorimetric assay and AMPPD the chemiluminescence assay. The chemiluminescence assay was over ten times as sensitive as the colorimetric assay.

EXAMPLE 2

Tandem Icon II hCG Assay (By Film Exposure)

Used a commercial Tandem ICON II assay kit (Hybritech, Inc.). Buffers and antibodies used were included in the kit and AMPPD was used as a substrate of alkaline phosphatase.

METHOD

Figure 2:
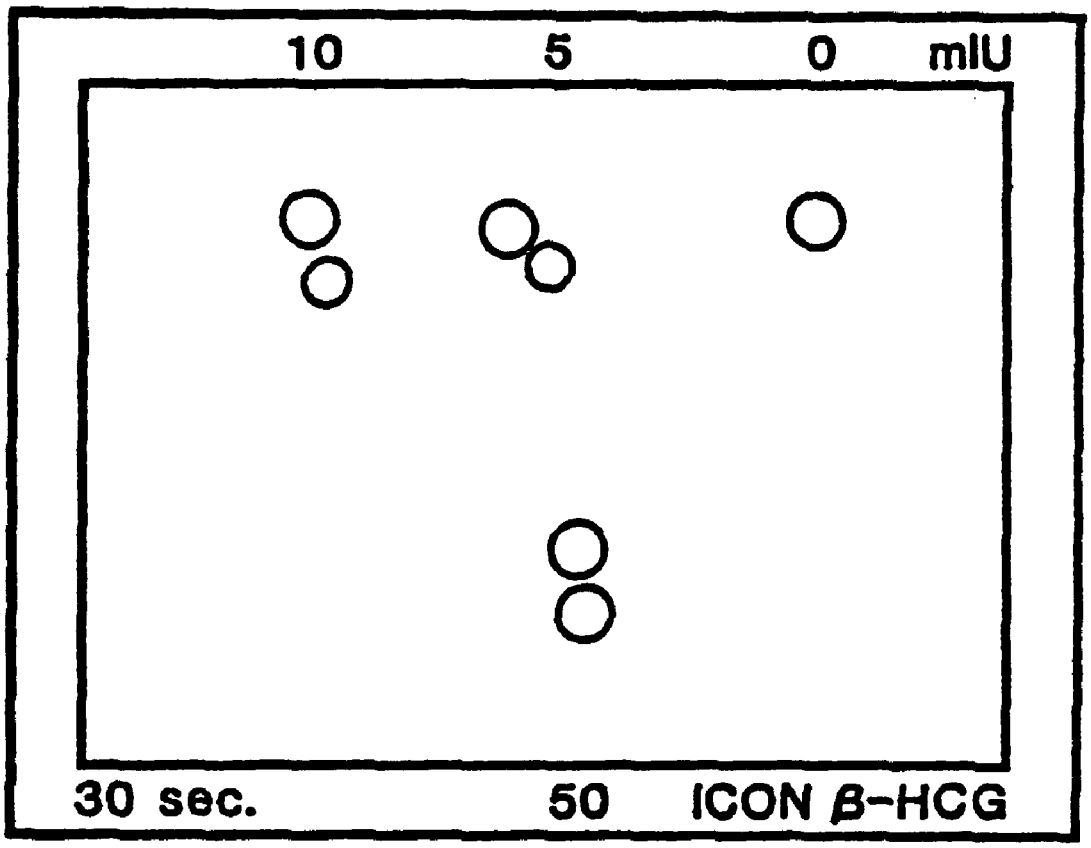
FIG. 2 shows the results of the solid state immunoassay for hCG of the invention using AMPPD as the lumogen and using film exposure for detection of the hCG.

1. Prepared hCG standards at 0, 5, 10, 50 mIU/ml diluted in control negative (male) urine for use as test samples.
2. Added 5 drops of the sample to the center of an ICON membrane device.
3. Added 3 drops of enzyme antibody conjugate to the center of each device.
4. Incubated for 1 minute.
5. Added 2 ml of Hybritech ICON wash solution to the device. Allowed to drain.
6. Added 500 μl of 0.1% BSA in 0.1 M Tris buffer, 1 mM $MgCl_2$, pH 9.8. Allowed to drain.
7. Added 200 μl of 50 μg/ml AMPPD in 0.1% BSA, 0.1 M Tris buffer, pH 9.8, 1 mM $MgCl_2$.
8. Transferred ICON membrane to a piece of Mylar polyester film and inserted into a black box to expose film. (Polaroid Type 612).
9. Exposed film for 30 seconds. The results of a typical assay are shown in FIG. 2. Intense chemiluminescence from positive samples occurred within a 30-second reaction time.

EXAMPLE 3

Alkaline Phosphatase Assay

An assay for alkaline phosphatase was conducted in the following manner.

COMPONENTS

Buffer: 0.05 M carbonate, 1 mM $MgCl_2$ at pH 9.5.

Substrate: 3-(2'-spiroadamantane)-4-methoxy-4-(3"-phosphoryloxy) phenyl-1,2-dioxetane disodium salt (AMPPD) at 0.4 mM concentration.

Alkaline Phosphatase: stock solution at 1.168 μg/ml in the buffer.

Serial dilutions of alkaline phosphatase stock solutions were made in tubes with final enzyme concentrations of: $4.17\times10^{-11}$M, $8.34\times10^{-12}$M, $1.67\times10^{-12}$M, $3.34\times10^{-13}$M, $6.68\times10^{-14}$M; $1.34\times10^{-14}$M, $3.34\times10^{-15}$M, $1.67\times10^{-15}$M, $8.34\times10^{-16}$M, $4.17\times10^{-16}$M, $2.09\times10^{-16}$M,

PROCEDURE

Duplicate tubes at each of the above concentrations of alkaline phosphatase also containing 0.4 mM AMPPD were incubated at 30° C., for 20 minutes.

After incubation, 30-second light integrals were measured in a Turner 20E Luminometer. The limits of detection of alkaline phosphatase is shown in Table II.

Figure 3:
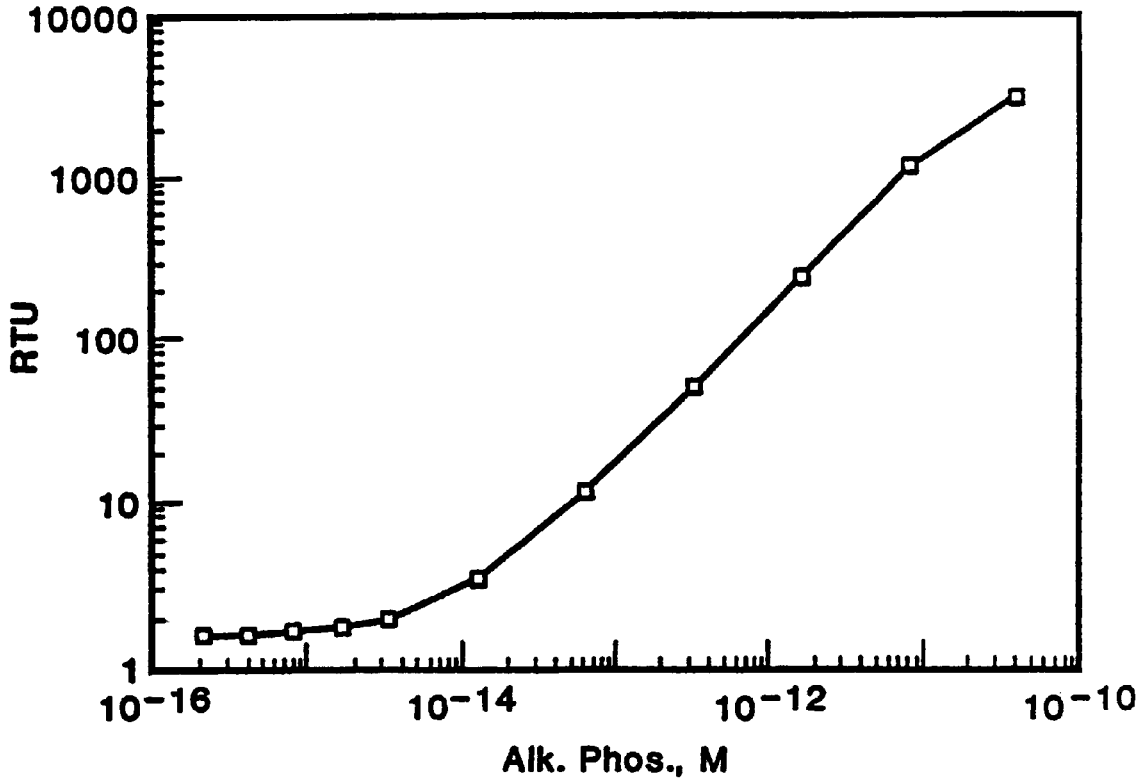
FIG. 3 is a standard curve for the quantitative estimation of the concentration of the enzyme alkaline phosphatase by the AMPPD chemiluminescence assay of the invention.

Data for the detection of alkaline phosphatase using 0.4 mM AMPPD is shown in FIG. 3. Light production was linear between $10^{-14}$ to $10^{-11}$ M enzyme.

TABLE II

| Addition | Concentration of Alkaline Phosphatase for 2× Background | Minimum Detectable Conc. of Alkaline Phosphatase |
|---|---|---|
| None | $1.0 \times 10^{-14}$ | $1.67 \times 10^{-15}$M(1.12) |

1. Buffer: 0.05 M sodium carbonate, 1 mM $MgCl^2$, pH 9.5, Temperature 30° C. AMPPD concentration was 0.4 mM.
2. The number in parentheses is the multiple of background at the indicated concentration.

EXAMPLE 4

Alkaline Phosphatase Assay in the Presence of Bovine Serum Albumin, BSA-Fluor, BDMQ and BDMQ-Fluor An assay for alkaline phosphatase was conducted in the following manner.

COMPONENTS

BUFFER: 0.05 M sodium carbonate, 1 mM $MgCl_2$, at pH 9.5.

Substrate 3-(2'-spiroadamantane)-4-methoxy-4-(3"phosphoryloxy)phenyl-1,2-dioxetane disodium salt (AMPPD) at 0.4 mM concentration.

Alkaline Phosphate: stock solution at 1.168 μg/ml in the buffer.

Conditions Tested:

1. Buffer alone, control.
2. Buffer plus 0.1% bovine serum albumin (BSA).
3. Buffer plus 0.1% BSA-fluorescein (BSA to fluorescein ratio 1 to 3).
4. Buffer plus 0.1% poly[vinylbenzyl(benzyldimethylammonium chloride)] (BDMQ).
5. Buffer plus 0.1% BDMQ and fluorescein (0.01 mg of fluorescein disodium salt mixed with 1 ml of BDMQ).

Serial dilutions of alkaline phosphatase stock solutions were made in tubes at the final enzyme concentrations of: $4.17\times10^{-11}$M, $8.34\times10^{-12}$M, $1.67\times10^{-12}$M, $3.34\times10^{-13}$M, $6.68\times10^{-14}$M, $1.34\times10^{-14}$M, $3.34\times10^{-15}$M, $1.67\times10^{-15}$M, $8.34\times10^{-16}$M, $4.17\times10^{-16}$M, $2.09\times10^{-16}$M, $1.0\times10^{-16}$M, $5.0\times10^{-17}$M, 2 $5\times10^{-17}$M.

PROCEDURE:

Duplicate tubes with alkaline phosphatase at concentrations described above also containing 0.4 mM AMPPD were incubated at 30° C. under various conditions. Test tubes were incubated for 20 minutes under conditions 1, 4 and 5, while incubated for 90 minutes under conditions 2 and 3.

Figure 4:
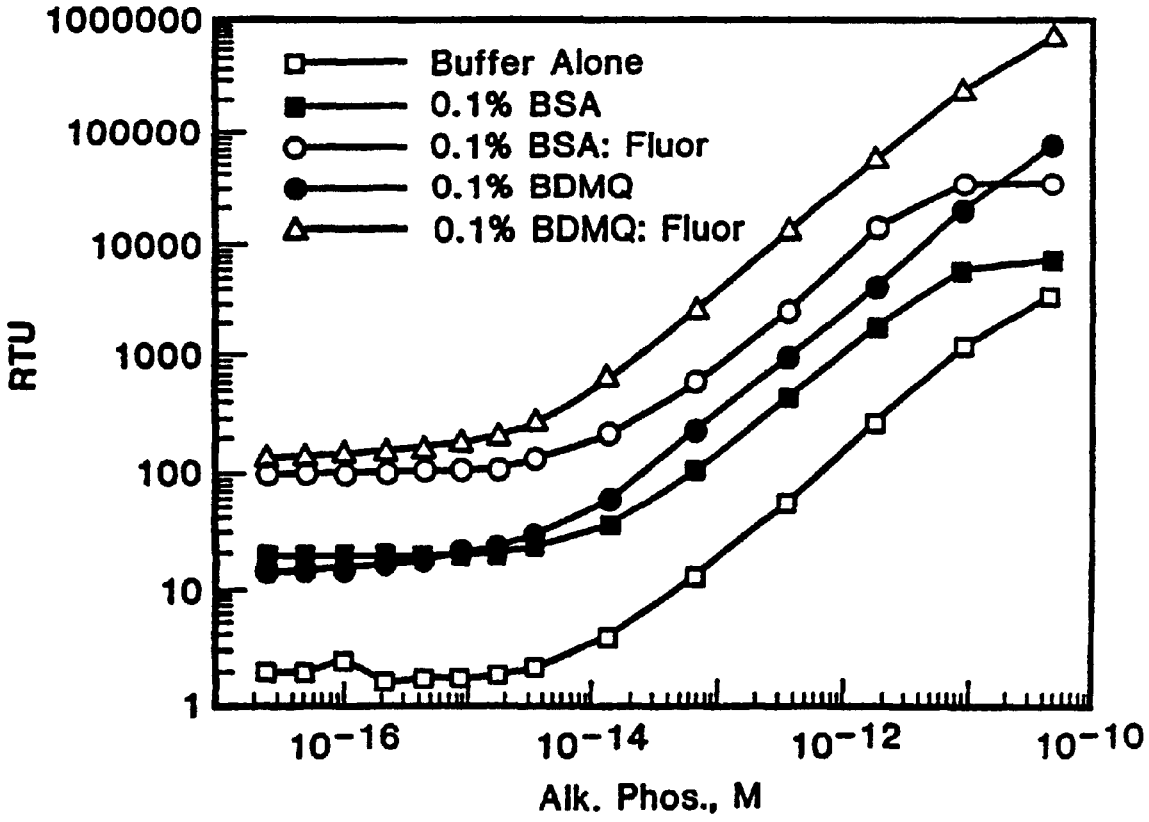
FIG. 4 compares the quantitative estimation of the concentration of the enzyme alkaline phosphatase by the AMPPD chemiluminescence assay of the invention in the presence and absence of bovine serum albumin (BSA), fluorescein (BSA-Fluor.) poly[vinylbenzyl(benzyldimethyl ammonium chloride)] (BDMQ), and BDMQ-Fluor.

After incubation, 30 second light integrals were measured in a Turner 20E Luminometer. The effect of BSA, BDMQ and fluorescein on the limits of detection of alkaline phosphatase is shown in FIG. 4 and Table III. In FIG. 4, —□—corresponds to results under condition 1 above: . . . ■ . . . condition 2: . . . ○ . . . condition 3; . . . ● . . . condition 4; and . . . Δ . . . condition 5, respectively.

TABLE III

| Addition | Concentration of Alkaline Phosphatase for 2× Background | Minimum Detectable Conc. of Alkaline Phosphatase |
|---|---|---|
| None | $1.0 \times 10^{-14}$ | $1.67 \times 10^{-15}$M (1.12)[1] |
| 0.1% BSA | $9.5 \times 10^{-15}$M | $8.34 \times 10^{-16}$M (1.06) |
| 0.1% BSA. Fluorescein | $1.3 \times 10^{-15}$M | $4.17 \times 10^{-16}$M (1.04) |
| 0.1% BDMQ | $4.0 \times 10^{-15}$M | $1.00 \times 10^{-16}$M (1.07) |
| 0.1% BDMQ: Fluorescein | $3.4 \times 10^{-15}$M | $2.09 \times 10^{-16}$M (1.06) |

[1]The number in parentheses is the multiple of background at the indicated concentration.

EXAMPLE 5

HSVI DNA Probe Assay

Materials and Buffers

Membrane: Gene Screen Plus, Positively charged nylon membrane.

Buffers:

Denaturation Buffer: 0.5 M NaOH

Neutralization Buffer: 0.4 M $NaH_2PO_4$ pH 2.0

Loading Buffer, 1 part Denaturation Buffer, 1 part Neutralization Buffer

Membrane Wetting Buffer: 0.4 M Tris buffer pH 7.5

Membrane Prehybridization Buffer:

| | Final Concentration |
|---|---|
| 0.5 ml 100 × Denhardt's solution | 5% |
| 0.5 ml 10% SDS | 0.5% |
| 2.5 ml 20 × SSPE | 5% |
| 2.0 mg denatured, sonicated salmon sperm DNA | 200 μg/ml |
| $ddH_2O$ | |
| 10 ml | |

| Membrane Hybridization Buffer: | Final Concentration |
|---|---|
| 0.5 ml 100 × Denhardt's solution | 5% |
| 0.5 ml 10% SDS | 0.5% |
| 2.5 ml 20 × SSPE | 5% |
| 2.0 mg salmon sperm DNA | 200 μg/ml |
| 2.0 ml 50% Dextran sulfate | 10% |
| $ddH_2O$ | |
| 10 ml | |

Wash Buffer I:

1 × SSPE/0.1% SDS
20 ml 20 × SSPE
4 ml 10% SDS
376 ml $ddH_2O$
400 ml

Wash Buffer II: 0.1 × SSPE/0.1% SDS preheated to wash temperature.

2 ml 20 × SSPE
4 ml 10% SDS
394 ml $ddH_2O$

-continued

| | |
|---|---|
| 400 ml (heated | |
| Wash Buffer III: | |
| 0.1 × SSPE/0.1% SDS | |
| 20 ml 20 × SSPE | |
| 4 ml 10% SDS | |
| 394 ml $ddH_2O$ | |
| 400 ml | |
| Wash Buffer IV: | |
| 3 mM Tris-HCl (pH 9.5) | |
| 0.6 ml IM Trizma Base | |
| 199.4 ml $ddH_2O$ | |
| 200.0 ml | |

Dissolved 2 g of polyvinylpyrrolidone mol. wt. 40K (PVP-40) and 2 g of Ficoll at temperatures greater than 65° C. but less than boiling. Cooled the solution to approximately 40° C., added 2 g of BSA and brought the final volume of 100 ml with $ddH_2O$. Aliquots were stored at −20° C.

| | |
|---|---|
| 20× SSC | |
| 20× SSC (for 100 ml) | |
| 3.0 M Sodium Chloride | 17.4 g |
| 0.3 M Sodium Citrate | 8.8 g |
| Bring volume to 100 ml and filter through a 0.45 μm nitrocellulose filter. Store at room temperature. | |
| 20× SSPE | |
| 20× SSPE pH 7.4 (for 1 liter) | |
| 3.6 M NaCl | 210.24 g |
| 200 mM Sodium phosphate 23 g dibasic | 5.92 g monobasic |
| 20 mM EDTA | 7.44 g |
| Dissolve, adjust pH to 7.4 with 5 N | NaOH |
| Bring volume to 1 liter and filter through a 0.45 μm nitrocellulose filter. | |
| 1× TE | |
| 1× TE buffer | 10 MM Tris (pH 7.0) |
| | 1 mM EDTA |
| | Autoclave |

Method

Figure 5A:
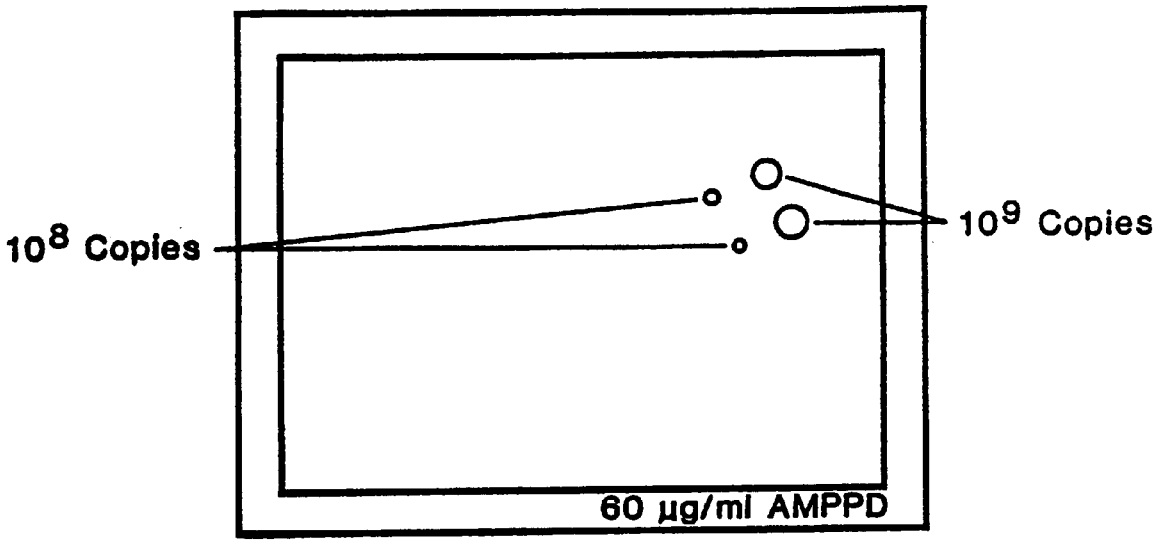
FIG. 5 shows the results of a Herpes Simplex Virus I (HSVI) DNA probe assay using a specific alkaline phosphatase-labeled ADNA probe in conjunction with the AMPPD chemiluminescence assay of the invention.
Figure 5B:
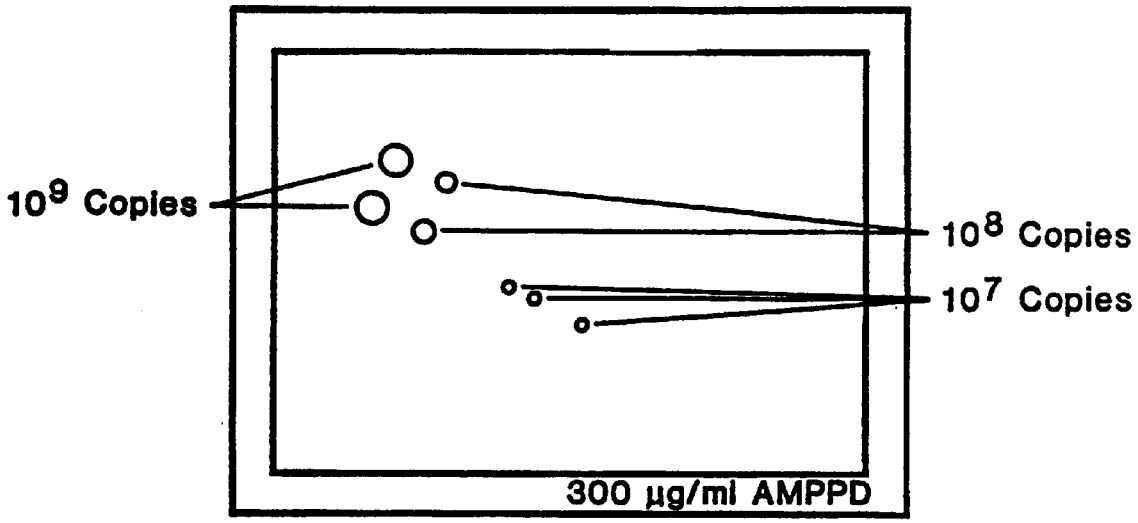
Figure 5C:
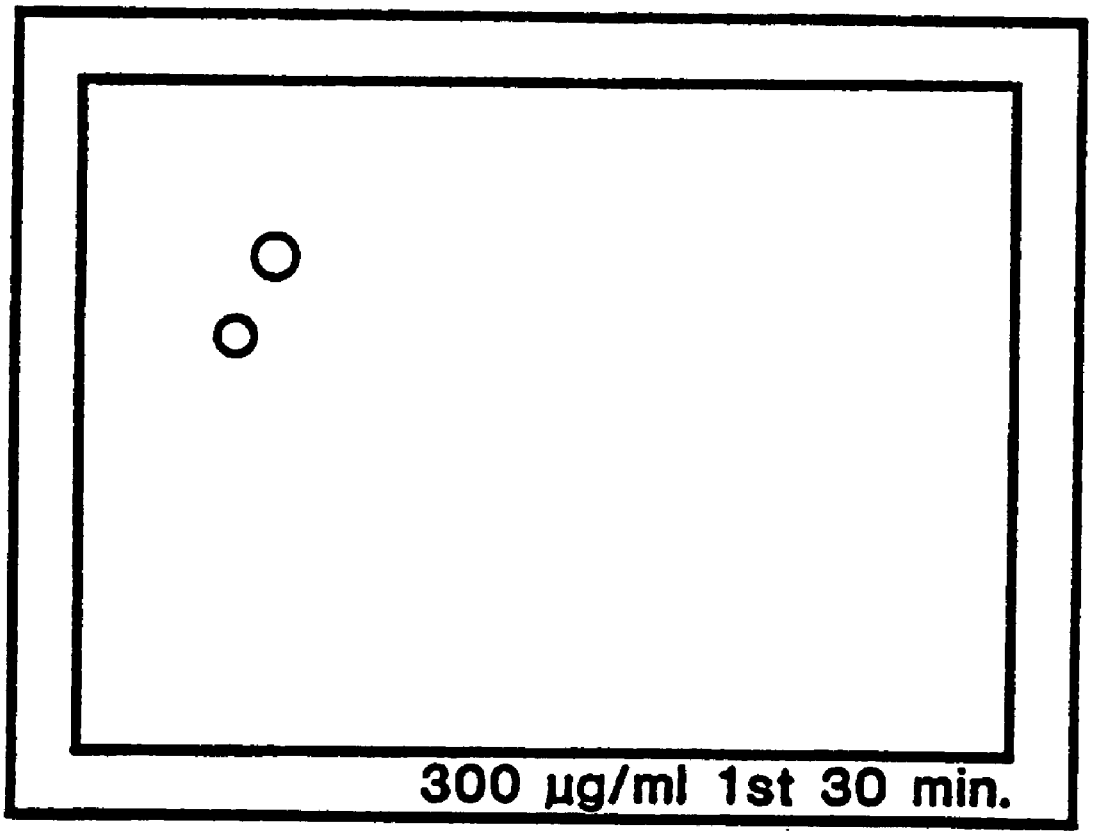

1. Prewetted membrane with Wetting Buffer for 15 min.
2. Inserted membrane into a vacuum manifold device.
3. Denatured the DNA sample by adding 50 μl of DNA sample (with known number of copies of HSVI DNA) to 200 μl of Denaturation Buffer. Incubated 10 min. at room temperature. Added 250 ml of ice cold Neutralization Buffer and kept denatured DNA on ice.
4. Added 200 μl of Loading Buffer to each well and aspirated through membrane.
5. Loaded denatured DNA samples to each well, and aspirated through membrane.
6. Repeated Step 4.
7. Dissembled manifold and removed membrane.
8. UV-fixed DNA to membrane using a UV Transilluminator for 5 minutes.
9. Incubated the membrane in 0.1% (w/v) BDMQ in phosphate-buffered saline for 15 minutes.
10. Incubated membrane in Prehybridization Buffer at 70° C. for 1 hour.
11. Added alkaline phosphatase-labeled SNAP probe specific for HSVI dissolved in Membrane Hybridization Buffer. Incubated for 3–5 hours at 70° C.
12. Removed membrane from Hybridization Buffer and incubated in 400 ml of Wash Buffer I, while agitating at room temperature for 10 minutes.
13. Washed with 400 ml of Wash Buffer II at 50° C. for 30 minutes.
14. Washed with 400 ml of Wash Buffer III at room temperature for 10 minutes.
15. Washed with 200 ml of Wash Buffer IV at room temperature for 10 minutes.
16. Added 2 ml of 300 μg/ml AMPPD in 0.1 M Tris buffer, 1 mM $MgCl_2$, pH 9.8 to the membrane.
17. Transferred the membranes to a piece of Mylar polyester film, and then to a black box containing Type 612 Polaroid film.
18. Exposed film for 30 minutes. Typical results are shown in FIG. 5, wherein FIG. 5A shows the results at 60 μg/ml AMPPD, FIG. 5B at 300 μg/ml AMPPD, and FIG. 5C after the first 30 min. of reaction at 300 μg/ml AMPPD.

EXAMPLE 6

Hepatitis B Virus DNA Hybridization Assay

We compared the sensitivity of a chemiluminescent substrate (AMPPD) and a chromogenic substrate (BCIP/NBT) for detection of an alkaline phosphate label in Hepatitis B Virus Core Antigen DNA $HBV_c$ probe hybridization assay (SNAP®, Dupont). Chemiluminescent signals obtained from AMPPD hydrolysis by said phosphatase was detected with Polaroid Instant Black and White Type 612 film.

Methods and Materials

1. Chemiluminescent Substrate: AMPPD
2. Protocol for Determining the Sensitivity of SNAP®/Test for $HBV_c$ (Hepatitis B "Core Antigen" DNA)

The levels of detection, or the sensitivity, of the SNAP® DNA probe test for Hepatitis B "Core Antigen" DNA were determined by performing the test using serially diluted $HBV_c$ control plasmid DNA.

The assay protocol involved the following steps:

a. Preparation of Positive $HBV_c$ DNA Plasmic Controls

A stock solution of $HBV_c$ plasmid was prepared by dissolving 100 ng ($1.2\times10^{10}$ copies) of the plasmid in 25 ul of sterile, deionized $H_2O$ and serially diluted with 0.3 N NaOH to produce plasmid samples in the concentrations range of $4.88\times10^3$–$0.96\times10^8$ a copies/ul. The samples were allowed to denature for 15 minutes at room temperature.

b. Preparation of the Membranes. Immobilization of $HBV_c$ Plasmid Control DNA

Gene Screen® Plus membranes were cut into 1×8 cm strips. 1 ul of each dilution of $HBV_c$ plasmid sample was spotted on the dry membrane with a pipette tip in contact with the membrane surface to obtain very small, concentrated spots. The membranes were then rinsed with 100 ul of 2 M ammonium acetate per spot to neutralize the target immobilized nucleic acid. They were subsequently rinsed with 0.6 M sodium chloride, 0.08 M sodium citrate, pH 7.0 buffer.

c. Probe Hybridization (i)-Prehybridization

The membranes containing plasmid samples were placed in a heat-sealable pouch in 3 ml of Hybridization Buffer. Prehybridization was carried out for 15 minutes at 55° C.

(ii)-Hybridization

SNAP® alkaline phosphatase labeled probe was reconstituted with 100 ul of the sterile deionized H20. The hybridization solution was prepared using 2.5 ul alkaline phosphatase labeled probe solution dissolved in 0.5 ml Hybridization Buffer. Hybridization was performed in a new, heat sealed pouch, with 0.5 ml hybridization solution, for 30 minutes at 55° C. After hybridization, the pouch was opened and the membranes carefully removed and washed with the following buffers:

1. twice with 0.1 M sodium chloride, 0.02 M sodium citrate, pH 7.0, plus 10 g SDS buffer, for 5 minutes at room temperature,
2 twice with 0.1 M sodium chloride, 0.02 M sodium citrate, pH 7.0, plus 10 ml Triton X-100 (Sigma Chemical Co., St. Louis, Mo.), for 5 minutes at 55° C.,
3. twice with the above buffer for 5 minutes at room temperature,
4. twice with 0.1 M sodium chloride, 0.02 M sodium citrate, pH 7.0 buffer for 5 minutes at room temperature,
5. once with 0.1% BSA in 0.05 M carbonate buffer at pH 9.5.

Hybridization Buffer was prepared by mixing 250 ml of 3 M sodium chloride, 0.4 M sodium citrate, pH 7.0, diluted to 800 ml with deionized $H_2O$, with 5 g Bovine Serum Albumin, 5 g polyvinylpyrrolidone (average MW 40,000) and 10 g SDS, warmed and mixed to dissolve.

d. Chemiluminescent Detection of $HBV_c$ Plasmid DNA with AMPPD

The hybridized membrane strips were saturated with 100 ul of 1.6 mM AMPPD in 0.1% BSA in 0.05 M carbonate Buffer, 1.0 mM $MgCl_2$ at pH 9.5. The membranes were then sealed in a plastic pouch and immediately placed in a camera luminometer where light emission was imaged on Polaroid Instant Black/White 20,000 ASA film.

e. Detection with SNAP® Chromogenic Substrates (Nitro Blue Tetrazolium (NBT) 5-Bromo-4-Chloro-3-Indoly Phospate (BCIP) (Performed According to the Manufacturer's Instructions)

Hybridized membranes which were developed with the chromogenic substrates did not undergo wash step #5. Substrate solution was prepared by mixing 33 ul NBT and 25 ul of BCIP in 7.5 ml of alkaline phosphatase substrate buffer provided by the manufacturer. Washed hybridized membranes were transferred to a heat sealed pouch with the substrates containing buffers. The color was allowed to develop in the dark, as NBT is light sensitive.

f. Photographic Detection of AMPPD Signal

The results of assays performed with AMPPD were imaged on Polaroid Instant Black and White Type 612 photographic film. The images were subsequently digitized using a black and white RBP Densitometer, Tobias Associates, Inc., Ivyland, Pa.

Results

Figure 6:
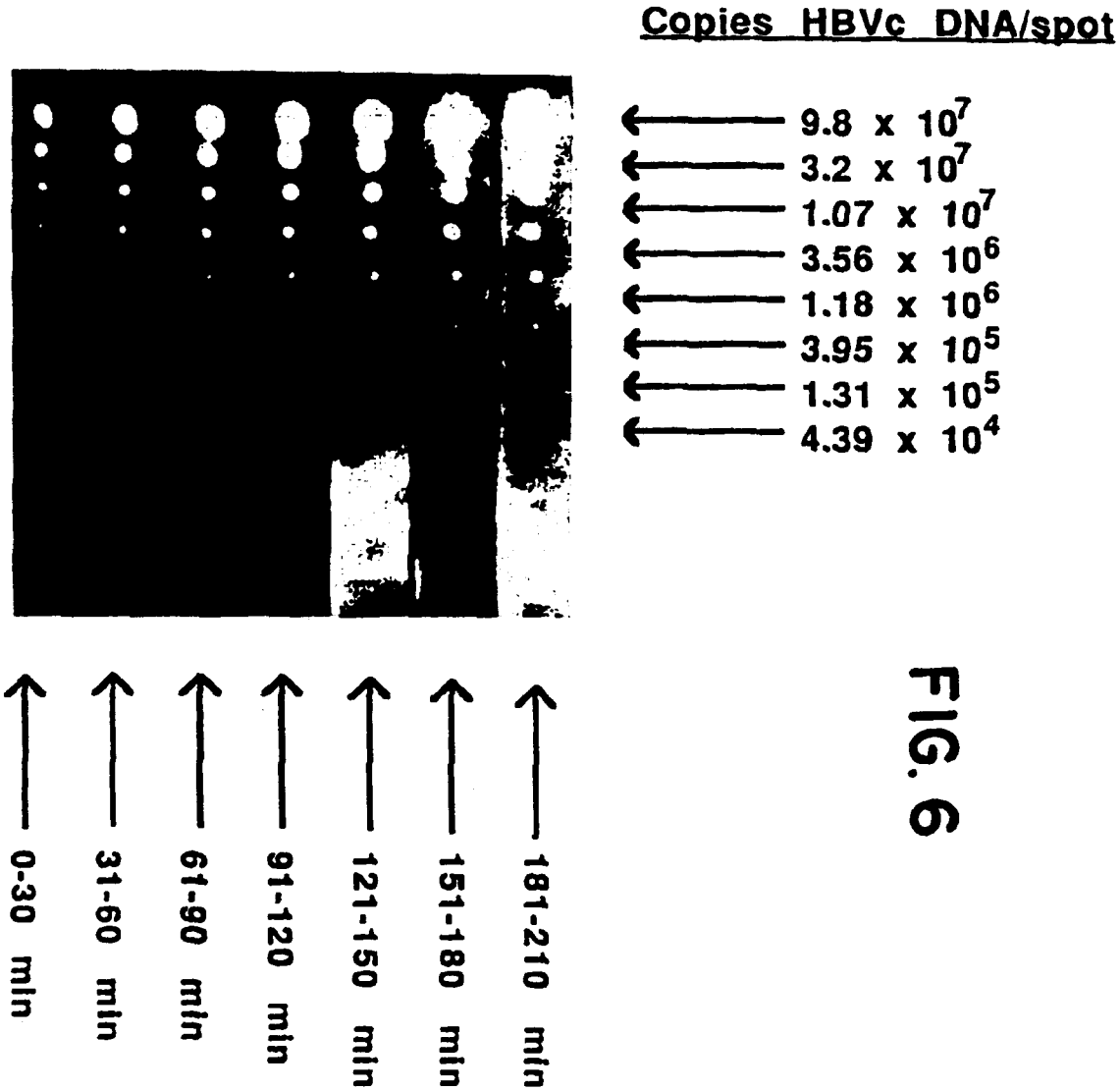
FIG. 6 shows the time course of the AMPPD chemiluminescence method of the invention applied to the hybridization-based detection of hepatitis B core antigen plasmid DNA ($HBV_c$) with an alkaline phosphatase-DNA probe conjugate, using a film detection technique.
Figure 7:
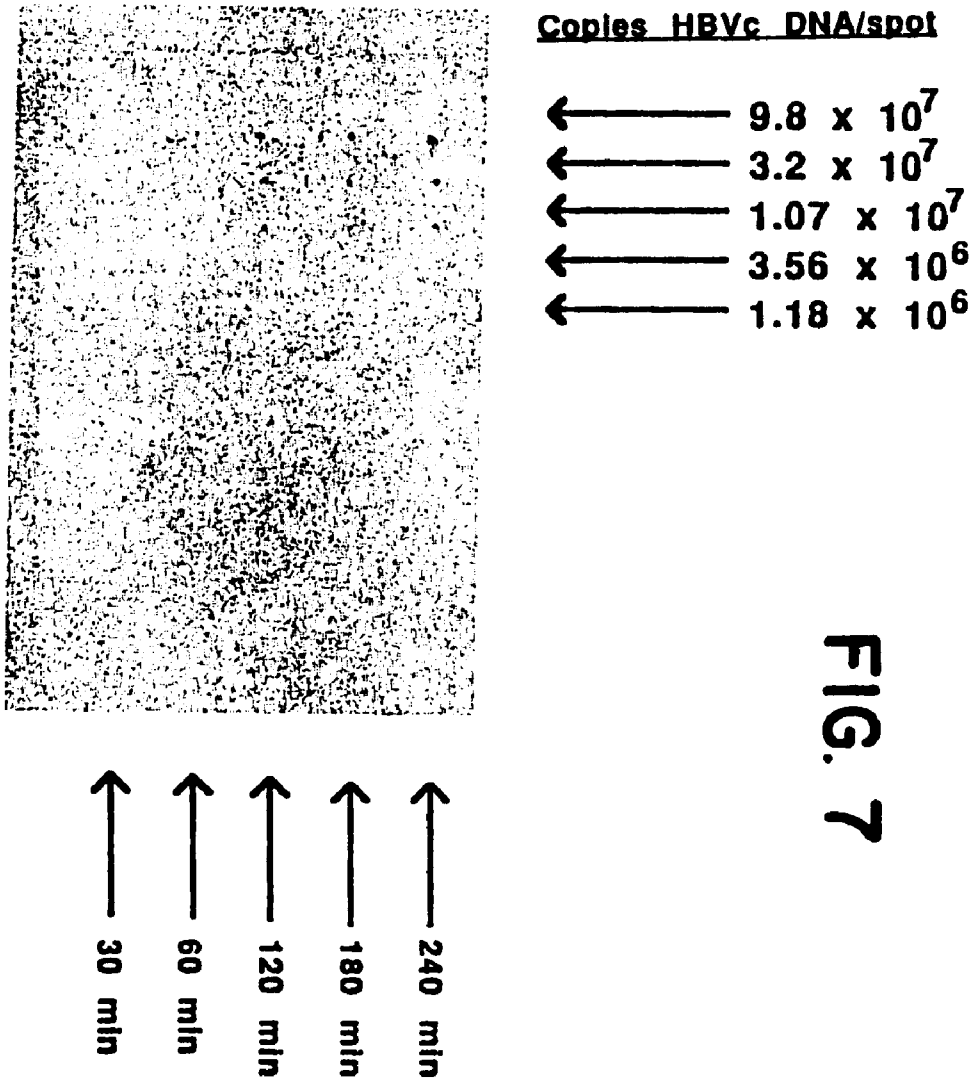
FIG. 7 shows the time course of the colorimetric detection of Hepatitis B core antigen plasmid DNA with an alkaline phosphatase-DNA probe conjugate using nitroblue tetrazolium (NBT)/5-bromo-4-chloro-3-indolyl phosphate (BCIP) as substrates.

FIG. 6 shows a time course of the chemiluminescent assay for serially diluted Hepatitis B Virus "Core Antigen" plasmid DNA hybridized with alkaline phosphatase labeled probe and imaged onto photographic film. Each photograph corresponds to a 30 minute exposure on Polaroid Instant Black and White Type 612 film. A comparable set of serially diluted Hepatitis B Virus "Core Antigen" plasmid DNA hybridized with alkaline phosphatase labeled probe and detected BCIP/NBT substrate is shown in FIG. 7. The chemiluminescent assay detected $1.18\times10^6$ copies of $HBV_c$ DNA. The colorimetric test showed a detection of $1.07\times10^7$ copies. After a two hour incubation, the chemiluminescent assay detected $4.39\times10^4$ copies of $HBV_c$ DNA. The colorimetric test showed a detection of $1.07\times10^7$ copies after the same incubation time. After a 4 incubation, the colorimetric assay detected $1.18\times10^6$ copies of $HBV_c$ DNA.

Table IV summarizes the results of chemiluminescent detection limits of $HBV_c$ using AMPPD and the colorimetric detection with BCIP/NBT substrates. Sensitivity of the SNAP® hybridization kit was improved over 100-fold using the chemiluminescent assay based upon AMPPD. The AMPPD-based assay detected as few as about 44,000 copies of $HBV_c$ plasmid DNA, compared to the BCIP/NBT colorimetric assay which required 10,700,000 copies for detection. In addition, AMPPD reduced the assay time from 4 hours to 30 minutes.

TABLE IV

Comparison of Detection Limits for Hepatitis B "Core Antigen" Plasmid DNA Using Chemiluminescent and Chromogenic Substrates in SNAP ® Hybridization Kit

| Copies of $BHS_c$ DNA Per Spot | Chemiluminescent AMPPD Substrate Detection in Minutes | Colorimeric BCIP/NBT Substrates Detection in Minutes |
|---|---|---|
| $9.8\times10^7$ | 30 | 30 |
| $3.2\times10^7$ | 30 | 60 |
| $1.07\times10^7$ | 30 | 120 |
| $3.56\times10^6$ | 30 | 180 |
| $1.18\times10^6$ | 30 | 240 |
| $3.95\times10^5$ | 60 | no color |
| $1.31\times10^5$ | 90 | no color |
| $4.39\times10^4$ | 120 | no color |

Figure 8:
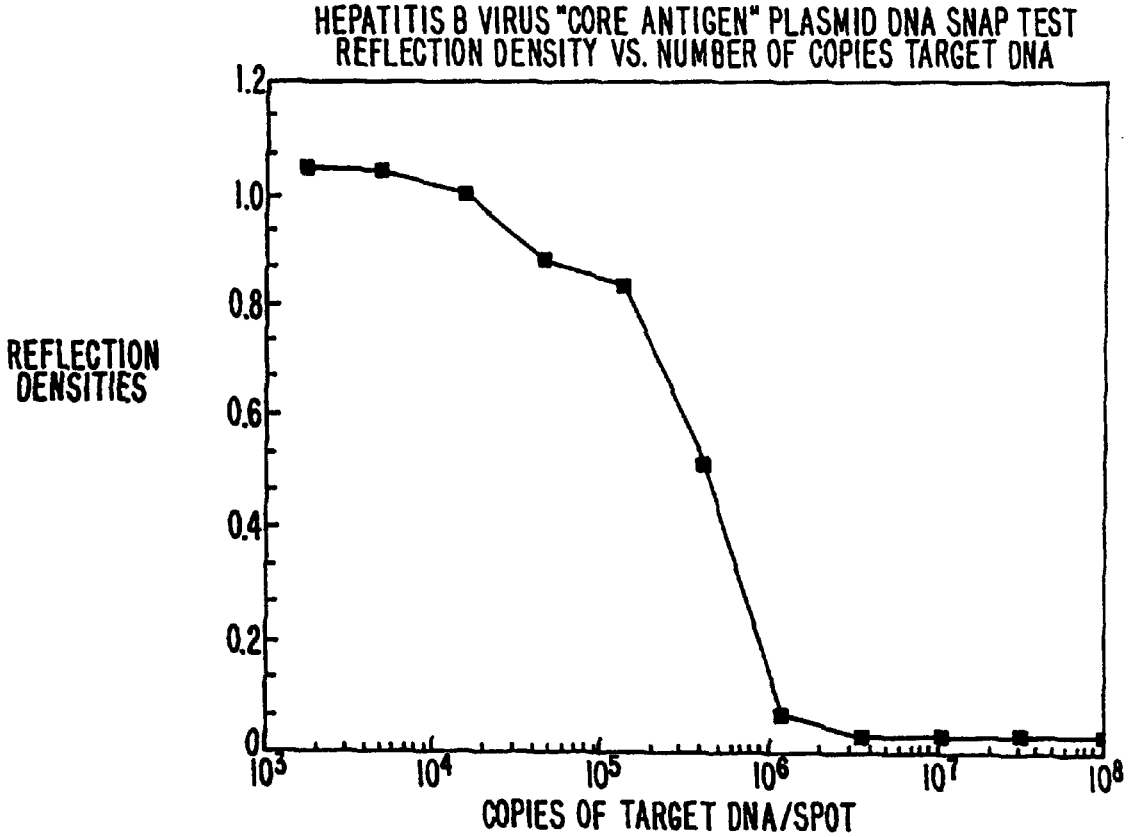
FIG. 8 shows the quantitative application of the assay of FIG. 6, wherein the film images were quantified by measuring reflection densities.

Quantitative chemiluminescence results could be obtained by measuring reflection densities directly from the imaged Black and White Polaroid Type 612 instant photographic film strips using a Tobias RBP Black and White Reflection Densitometer, as shown in FIG. 8. The results show that a dose response curve can be generated of the reflection densities as a function of $HBV_c$ plasmid concentration. This dose response curve can be subsequently used as a calibration for the determination of $HBV_c$ DNA levels in clinical specimens.

EXAMPLE 7

Bead Format AFP Elisa Assay for Alpha Feto Protein (AFP).

Anti-AFP antibody coated beads and anti-AFP antibody: alkaline phosphatase conjugates were obtained from a Hybritech Tandem Assay kit.

1. To each tube was added 20 $\mu$l of sample. Samples were 0, 25, 50, 100, and 200 mg/ml AFP.
2. Placed one bead in each tube.
3. Added 200 $\mu$l of anti-AFP antibody alkaline phosphatase conjugate to each tube.
4. Shook rack to mix contents of tubes.
5. Covered tubes.
6. Incubated for 2 hours at 37° C.
7. Aspirated off antibody and sample to waste.
8. Washed beads 3 times with 2.0 ml of.0.1% Tween 20 in phosphate buffered saline, pH 7.4.

| | For Colorimetric Assay | | Chemiluminescence |
|---|---|---|---|
| 9. | N/A | 9. | Washed 1 time with 0.5 M carbonate, 1 mM $MgCl_2$ pH 9.5. |
| 10. | Added 200 $\mu$l of 1 mg/ml p-nitrophenyl-phosphate (PNPP) glycine 1 mM $MgCl_2$ pH 10.4 | 10. | Added 2.50$\mu$ of 0.4 mM AMPPD in 0.05 M in 0.1 carbonate, 1 mM $MgCl_2$ pH 9.5 |

-continued

| | For Colorimetric Assay | | Chemiluminescence |
|---|---|---|---|
| 11. | Incubated for 30 minutes at room temperature | 11. | Incubated for 20 minutes at 30° C. |
| 12. | Added 1.5 ml of 0.1 M glycine, 10 mM EDTA, pH 9.5 to stop color development | 12. | N/A |
| 13. | Read in absorbance at 410 mm in spectrophotometer | 13. | Read 10 sec. integral of each tube in Turner luminometer |

Figure 9:
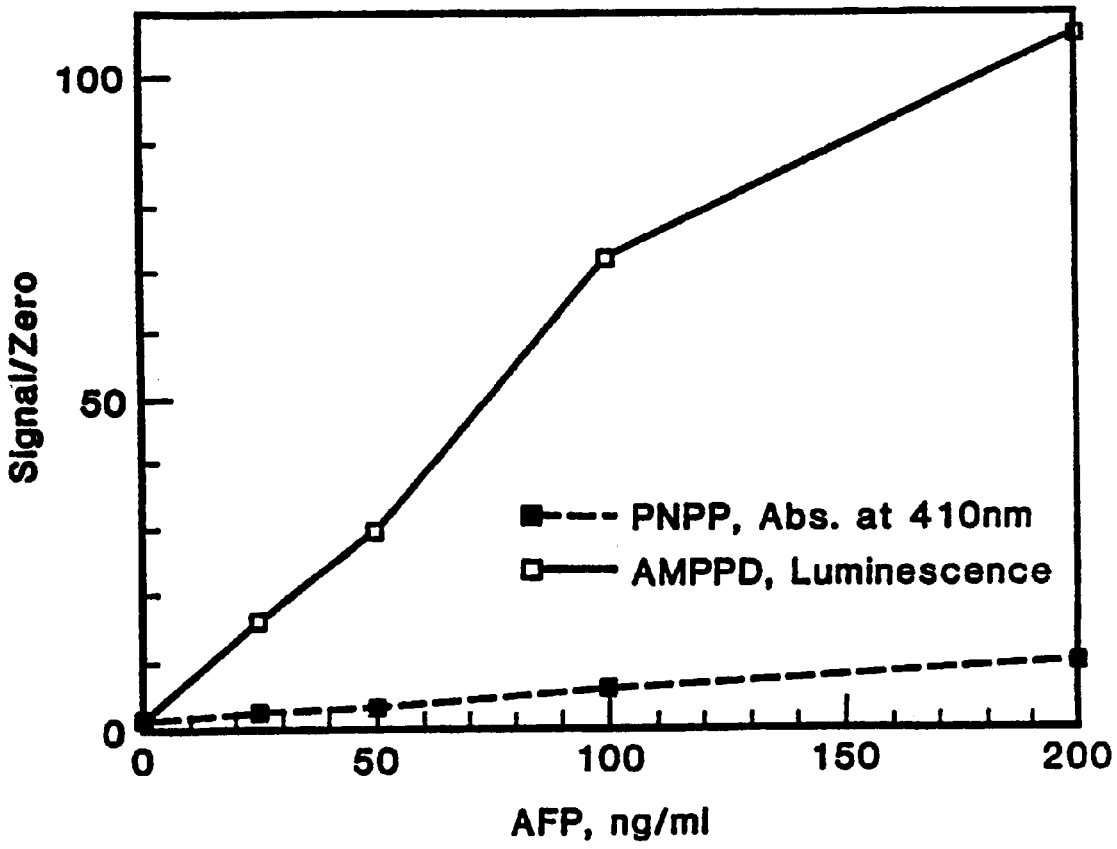
FIG. 9 compares a solid state ELISA method for alpha feto protein (AFP) using PNPP as a colorimetric substrate and the AMPPD chemiluminescence method of the invention for the quantitative estimation of AFP, wherein alkaline phosphatase is covalently linked to anti-AFP antibody.

14. Plotted both sets of data as the signal at each concentration of AFP divided by the signal at zero AFP vs. concentration of AFP. As shown in FIG. 9, the results of the colorimetric assay are shown in the PNPP curve, and that of the chemiluminescence assay in the AMPPD curve. It can be seen that the latter assay is about 10 times as sensitive as the former assay.

EXAMPLE 8

Assay for Thyroid Stimulating Hormone (TSH)

Materials

Mouse monoclonal anti-TSH-β antibody was used to coat ⅛ inch beads for analyte capture. Mouse monoclonal anti-TSH antibody was conjugated with alkaline phosphatase and used as a detection antibody (antibody- enzyme conjugate).

TSH was obtained from Calbiochem, Catalog No. 609396, and BSA (type V—fatty acid free) was obtained from Sigma, Catalog No. A6003.

The buffer solution used for the analyte and antibody enzyme conjugate contained 0.1 M Tris-HCl, 1 mM $MgCl_2$, and 2% by weight BSA (pH 7.5). The substrate buffer solution contained 0.1 M Tris, 0.1 mM $MgCl_2$, (pH 9.5), and the substrate AMPPD (50 μg/ml)

PROTOCOL

A TSH-containing analyte solution (15 μl) was mixed with 135 μl of antibody enzyme conjugate solution. Two ⅛ inch beads coated as described above were added to the solution and incubated for 2 hours at 23° C. The beads were then washed four times with 0.1 M Tris buffer (pH 7.5) and transferred to a reaction tube. 200 μl of the buffer solution containing the substrate described above was added to the tube. Following an incubation period of 20 minutes, light emission was recorded as ten second counts using a Berthold Clinilumat Luminescence Analyzer.

Figure 10:
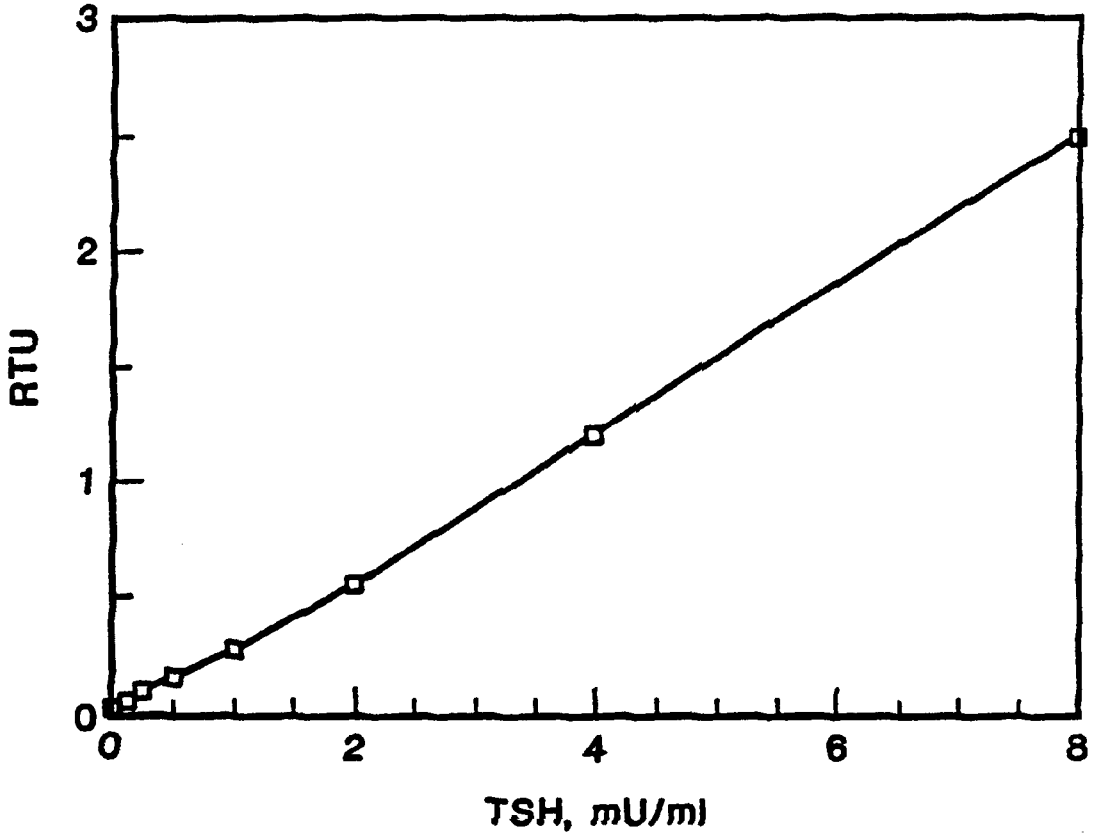
FIG. 10 shows a solid state monoclonal antibody ELISA for thyroid stimulating hormone (TSH) using the AMPPD chemiluminescence method of the invention wherein monoclonal anti-β-TSH antibody conjugated to alkaline phosphatase was used as the detection antibody.

FIG. 10, which is a plot of the data in Table V below, shows luminescence intensity for a given TSH concentration. Linearity was achieved between 1 and 8 μU/ml of TSH.

TABLE V

| TSH Concentration (μU/ml) | (Counts/10 sec × $10^{-4}$) |
|---|---|
| 1 | 0.25 |
| 2 | 0.49 |
| 4 | 1.1 |

Figure 11:
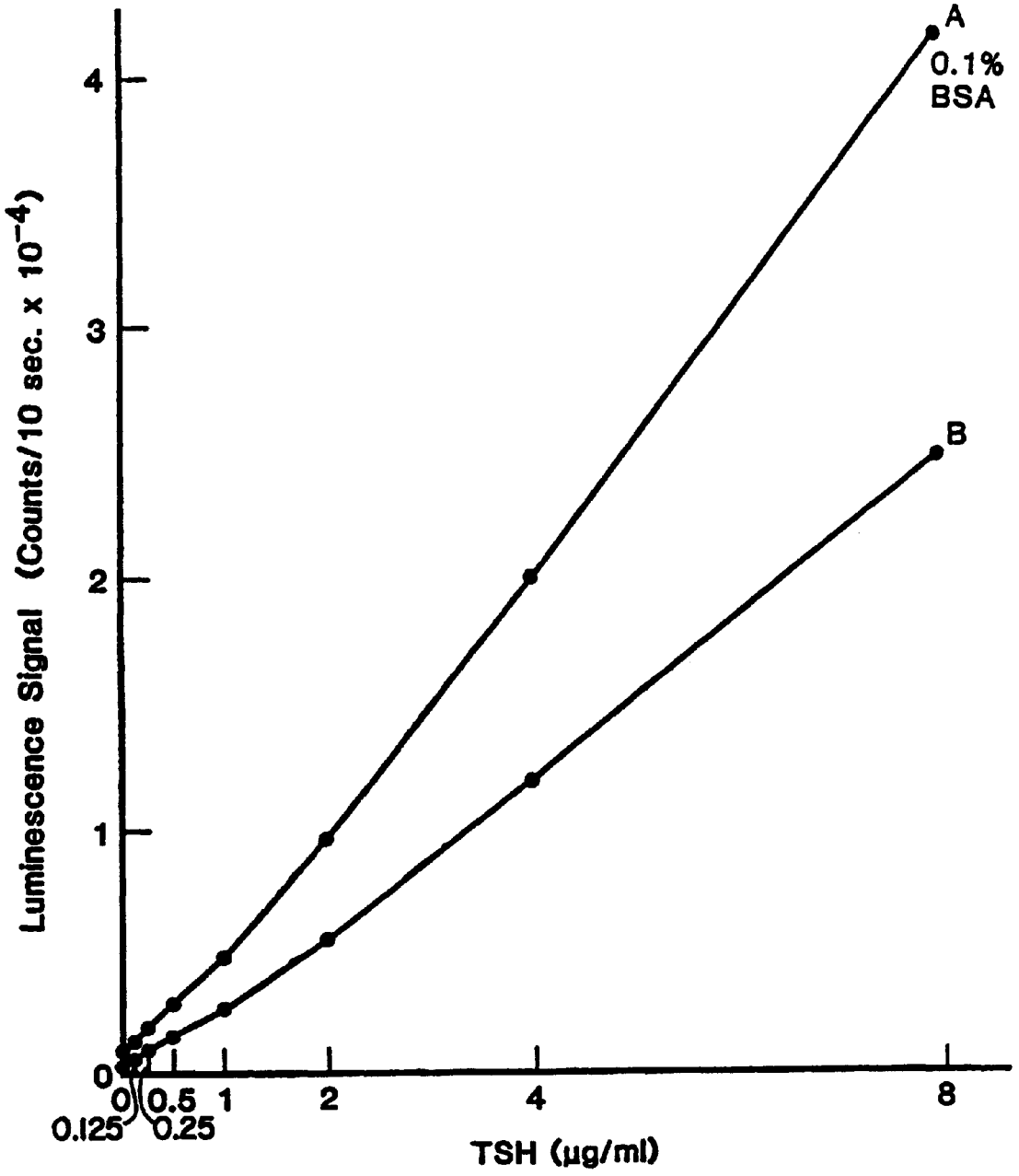
FIG. 11 represents the assay of FIG. 10 carried out both in the absence and presence of BSA.

An identical TSH assay was also performed in the absence of BSA for the sake of comparison. As shown in FIG. 11, the BSA-containing sample (Curve A) showed greater luminescence intensity for a given TSH concentration than the sample without BSA (Curve B).

EXAMPLE 9

Assay for Carcinoembryonic Antigen (CEA) in the Bead Format

Anti-CEA coated beads and anti-CEA antibody: alkaline phosphatase conjugates were obtained from a Hybritech Tandem Assay kit.

Figure 12:
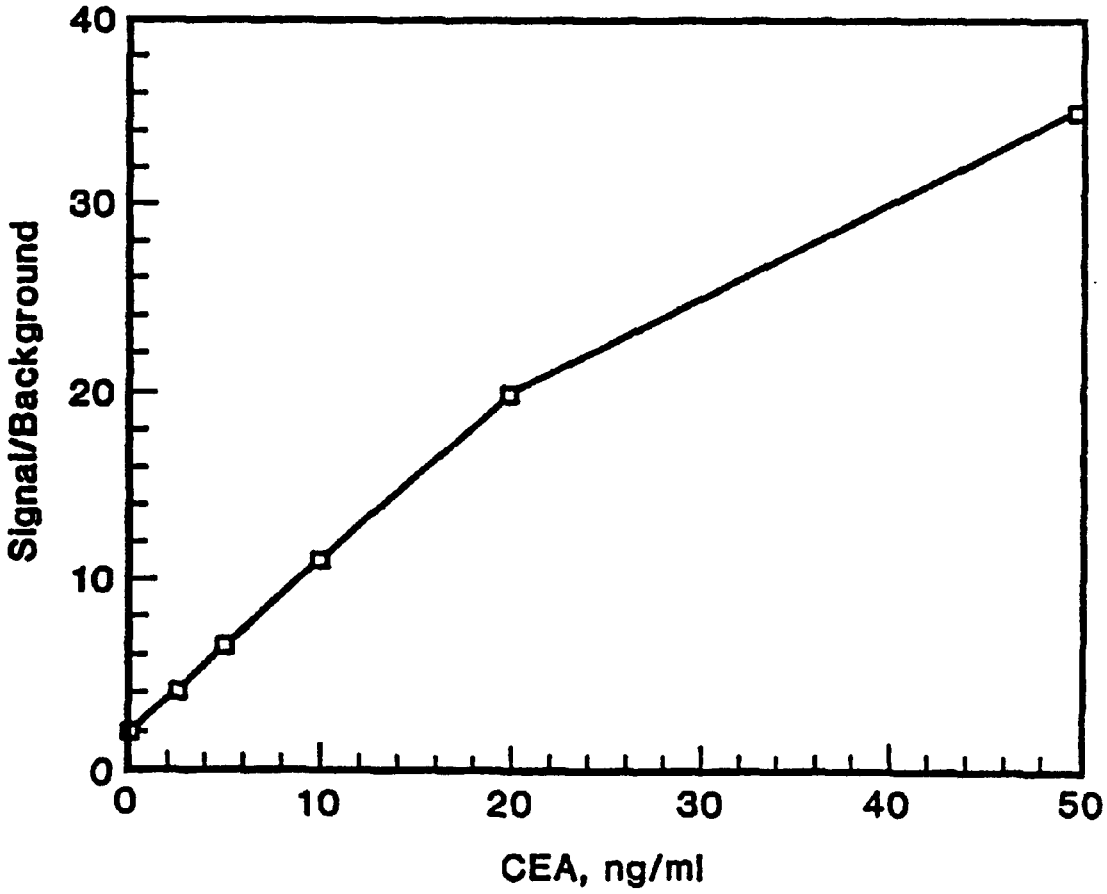
FIG. 12 shows the application of a solid state ELISA to the estimation of carcinoembryonic antigen (CEA), wherein α-CEA antibody-alkaline phosphatase was the detection antibody and the AMPPD chemiluminescence method of the invention was used to quantify the CEA.

1. To each tube were added 20 μl of sample. Standards of 0, 2.5, 5, 10, 20, and 50 ng/ml CEA were used.
2. One bead was placed in each tube.
3. Added 200 μl of anti-CEA antibody enzyme conjugate to each tube.
4. Shook rack to mix contents of tubes.
5. Covered tubes.
6. Incubated for 2 hours at 37° C.
7. Aspirated off antibody and sample to waste.
8. Washed beads 3 times with 2.0 ml of 0.1% Tween 20 in phosphate buffered saline, pH 7.4.
9. Washed once with 0.05 M sodium carbonate, 1 mM $MgCl_2$, pH 9.5.
10. Added 250 μl of 0.4 mM AMPPD in 0.05 M sodium carbonate, 1 mM $MgCl_2$, pH 9.5.
11. Incubated for 20 minutes at 30° C.
12. Read 10 sec. integral of luminescence from each tube in Turner 20E Luminometer.
13. Plotted both sets of data as the signal at each concentration of hCG divided by the signal at zero CEA vs. concentration of CEA. Typical data for a CEA assay using AMPPD are shown in FIG. 12. Linearity was achieved between 0 and 20 ng/ml of CEA.

EXAMPLE 10

Assay for Human Luteinizing Hormone (hLH)

Figure 13:
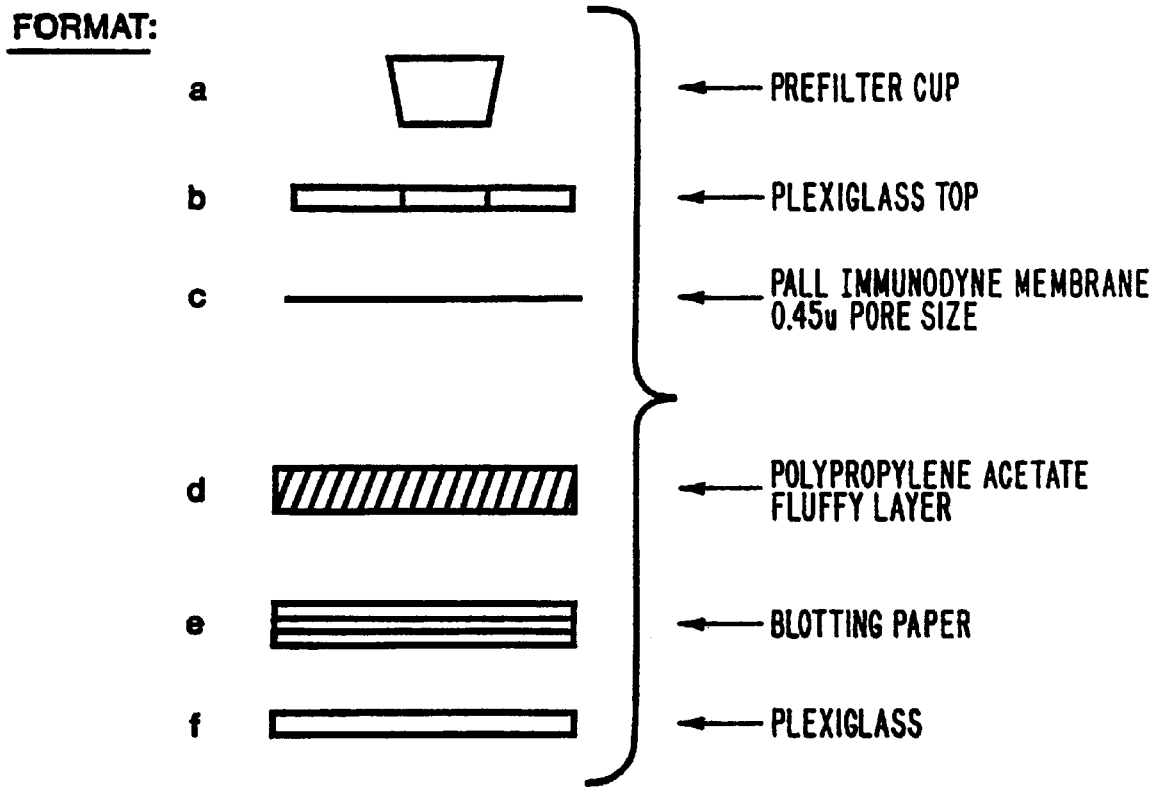
FIG. 13 is a diagram of the device used for the solid state immunoassay for human luteinizing hormone (hLH).

A nylon membrane, (Pall Immunodyne, 0.45 micron pore size), approximately 3 mm in diameter wa sensitized with 5 μl of a solution of 1 μg/ml of capture monoclonal anti-LH antibodies for solid phase in phosphate buffered saline (PBS), purchased from Medix, catalog #L-461-09. The membrane was subsequently blocked with 2% casein in phosphate buffered saline at pH 7.3. The membrane was then enclosed in the device shown in FIG. 13, which included blotting paper layers. In FIG. 13, A shows the prefilter cup; B plexiglass top; C Pall Immunodyne membrane (pore size 0.45 μ); D polypropylene acetate fluffy layer; E blotting paper; and F plexiglass.

The detection antibody used was mouse monoclonal anti-LH, purchased from Medix, catalog #L-461-03. This antibody was derivatized with alkaline phosphatase, (purchased from Biozyme, catalog #ALPI-11G), using the glutaraldehyde coupling procedure [Voller, A. et.al., Bull. World Health Org., 53, 55 (1976)].

Procedure

The detection antibody conjugate (50 μl) was added to tubes containing 200 μl of hLH of the following concentrations:

| Tube # | Conc. hLH in ng/ml of PBS |
|---|---|
| 1 | 0 |
| 2 | 1 |
| 3 | 10 |

-continued

| Tube # | Conc. hLH in ng/ml of PBS |
|---|---|
| 4 | 100 |

Figure 14:
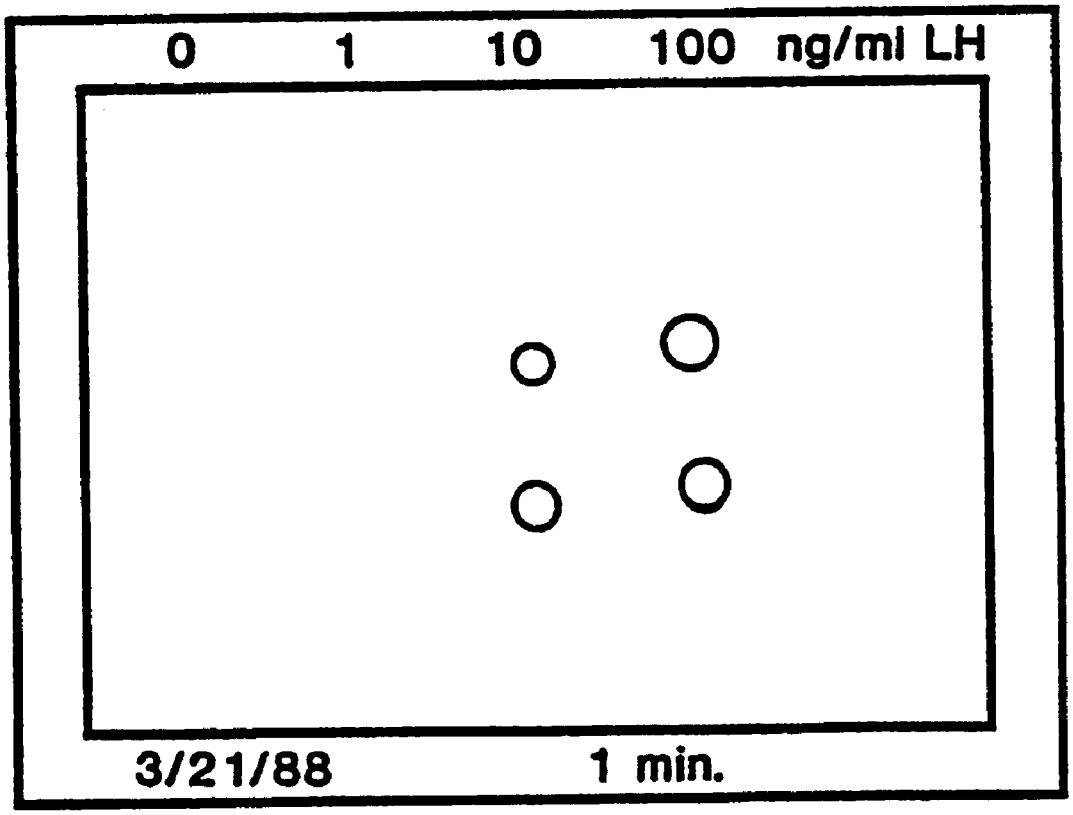
FIG. 14 shows the assay images on film for a solid state immunoassay for hLH wherein monoclonal anti-hLH antibody-alkaline phosphatase is the detection antibody and the AMPPD chemiluminescence assay of the invention was used to detect the hLH antigen.

The content of each tube was then added to four nylon membranes previously derivatized with capture antibodies (described above). After a five minute incubation period, the prefilter cup was removed and the membranes were washed with 400 μl of 0.05% Tween 20 in PBS. Subsequently, 100 μl of 0.4 mM AMPPD, in 0.05 M carbonate, 1 mM $MgCl_2$, 0.1% by weight BSA at pH 9.5 were added. The nylon membranes were placed in a camera luminometer containing type 612 Polaroid Instant Black and White film, and exposed for one minute. The results of the assay imaged on film are shown in FIG. 14.

Figure 15:
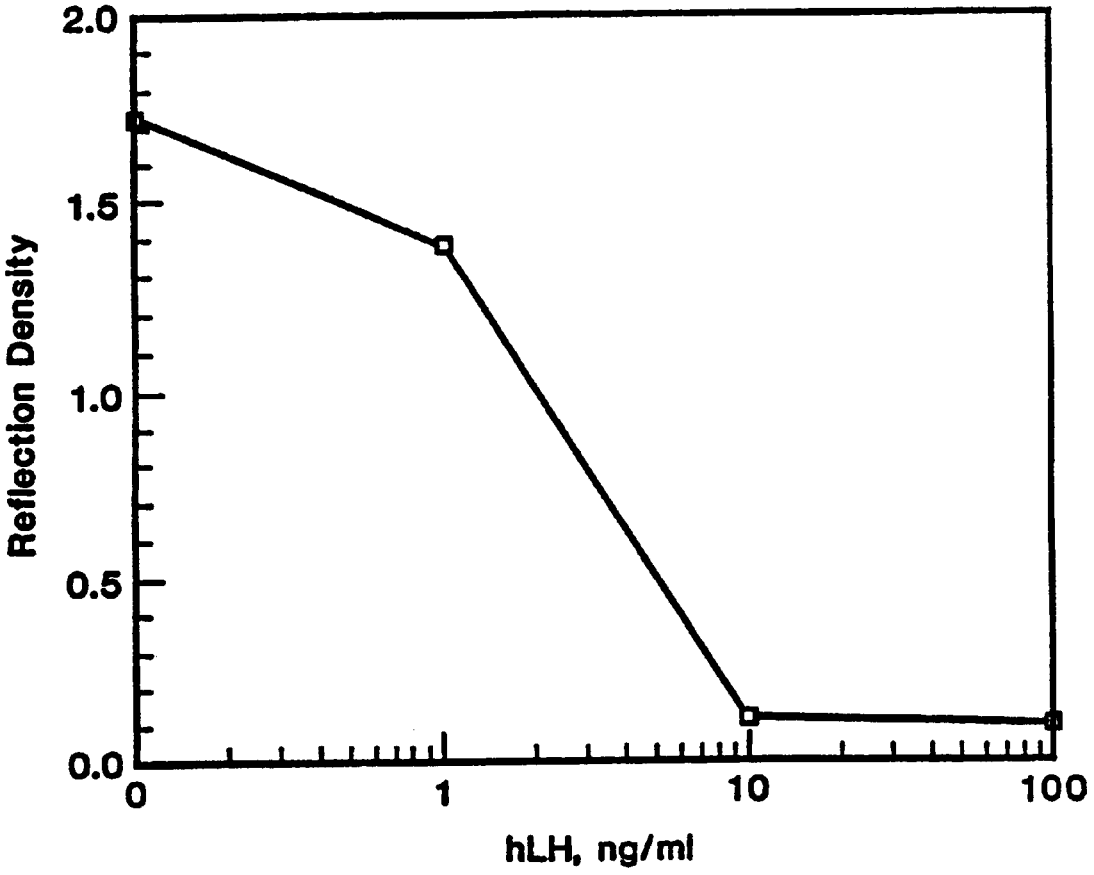
FIG. 15 shows a standard curve obtained for hLH wherein the film images obtained by the method of FIG. 14 were quantified by reflection density determinations at each concentration of hLH.

Subsequently, the reflection densities of the images were measured using the Tobias RBP Portable Black and White Reflection Densitometer (manufactured by Tobias Associates, Inc., 50 Industrial Drive., P.O. Box 2699, Ivyland, Pa. 18974-0347). The reflection densities were plotted versus concentration of LH to yield a standard curve for hLH, as shown in FIG. 15.

EXAMPLE 11

Chemiluminescent Decomposition of 3-(2'spiroadamantane)-4-methoxy-4-(3"β-D-galactopyranosyl-phenyl)-1,2-dioxetane (AMPGD)

Reagents

1. AMPGD synthesis as described above was made up in 1:1 $MeOH/H_2O$ at a concentration of 10 mg/ml.

2. 0.01 M sodium phosphate buffer, pH 7.3, containing 0.1 M NaCl and 1 mM $MgCl_2$.

3. β-Galactosidase (Sigma Chem. Co., catalog G5635, mol. wt. 500,000), 1 mg/ml in phosphate-salt buffer, pH 7.3, diluted 1:100 to yield a $2\times10^{-8}$ M solution.

Protocol

AMPGD solution (9.3 μl) was diluted in 490 μl of a buffer solution of variable pH. Subsequent addition of 5 μl of the diluted β-galactosidase solution was followed by 1 hr. incubation at 37° C. The final concentration of reactants was 0.4 mM AMPGD and $1\times10^{-13}$ moles β-galactosidase, at various pH values, as required by the experiment.

After incubation, the solutions were activated in a Turner 20E Luminometer by the addition of 100 μl of 1 N NaOH. The instrument temperature was 29° C., that of the NaOH room temperature.

Thus, the assay consisted of a two-step process wherein the substrate-enzyme incubation was performed at various pH values appropriate to efficient catalysis, e.g., at pH 7.3, and subsequently the pH was adjusted to about 12 with NaOH, and luminescence was read again.

Results

Figure 16:
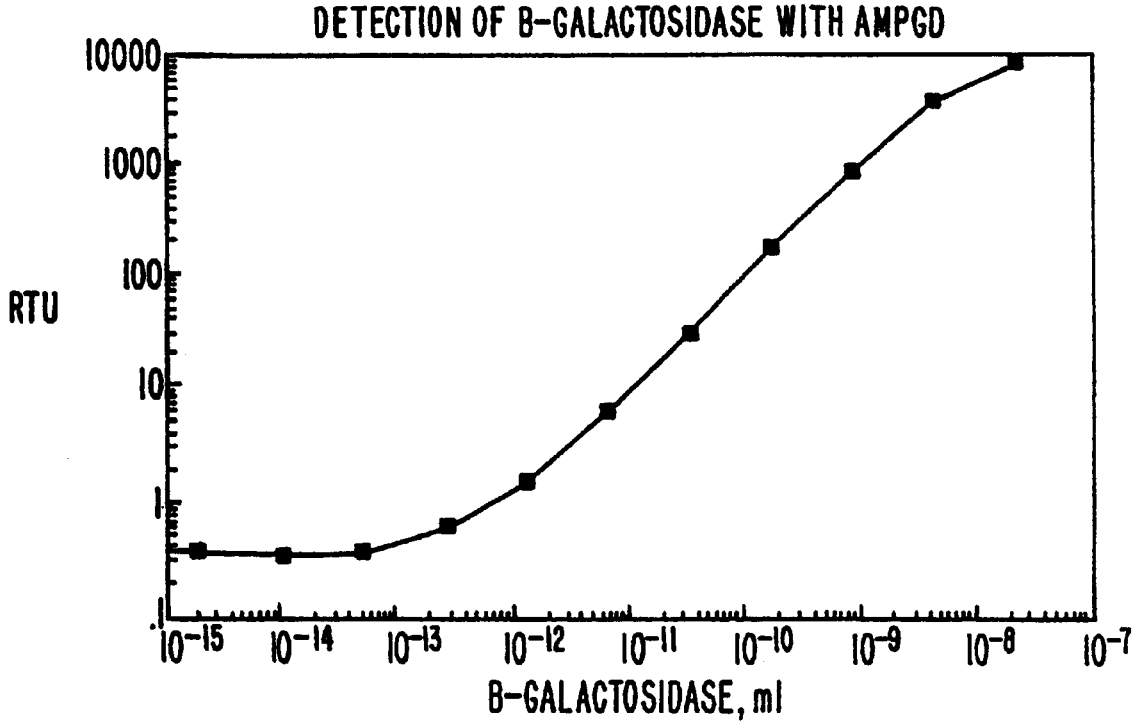
FIG. 16 shows a plot of chemiluminescence as a function of α-galactosidase concentration in the chemiluminescence assay of the invention wherein the substrate for the enzyme is 3-(2'-spiroadamantane)-4-methoxy-4-(3"-β-D-galactopyranosyl)phenyl-1,2-dioxetane (AMPGD).

In FIG. 16 is shown the chemiluminescence of a fixed concentration of AMPGD as a function of β-galactosidase concentration, wherein the enzyme reaction was run at pH 7.3 and luminescence measured at pH 12. The useable, i.e., linear, portion of the standard curve was at enzyme concentrations between $10^{-13}$ and $10^{-8}$ M.

Figure 17:
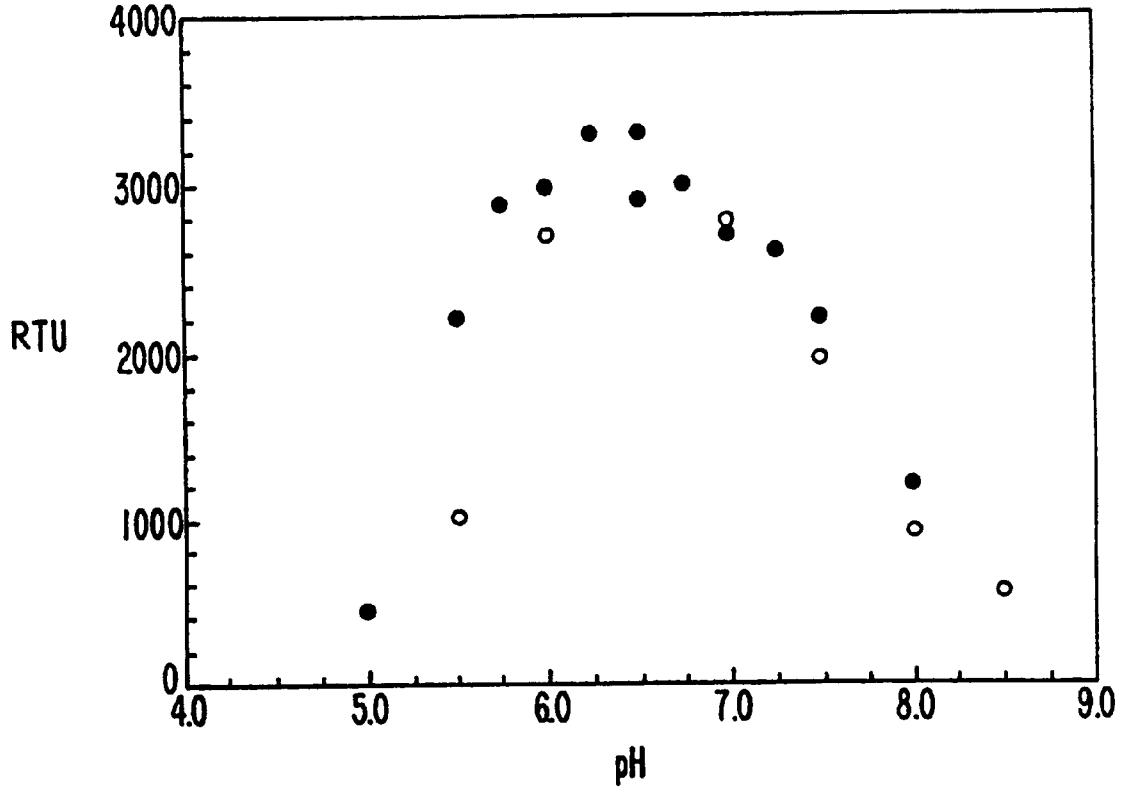
FIG. 17 shows the pH dependence of β-galactosidase-activated chemiluminescence from AMPGD.

In FIG. 17 is shown the effect of pH on the decomposition of AMPGD by β-galactosidase. The data show that the optimum pH for the enzyme with this substrate is about pH 6.5.

Figure 18:
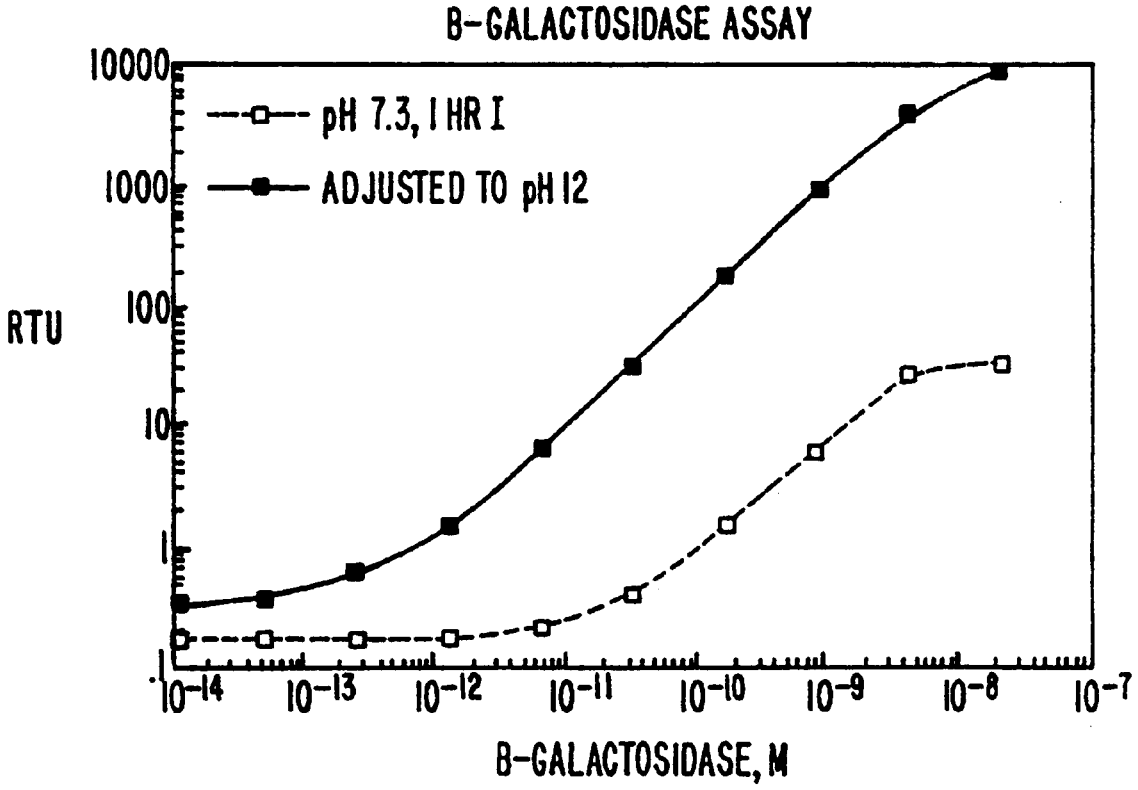
FIG. 18 shows the production of light by β-galactosidase decomposition of AMPGD wherein the light intensity was measured after enzyme incubation at a pH of 7.3 and adjusting the pH to 12 with alkali.

FIG. 18 shows the production of light from AMPGD as a function of β-galactosidase concentration, using the two-step protocol described above. At all enzyme concentrations, adjustment of the pH to 12 from 7.3 produced over a 100-fold increase in chemiluminescence.

EXAMPLE 12

Detection of DNA Fragments by Chemiluminescence After Electrophoretic Separation of Fragments DNA sequencing was performed using the dideoxy chain termination method of Sanger et al. (1977) above.

Biotinylated pBR322 primer (40 ng) was annealed to 5 μg of denatured pBR322 plasmid. Klenow Fragment (DNA polymerase I), 2 units, was then added (final volume was 17 μl). Subsequently, 2 μl of this template - primer solution was used for each of four base-specific reactions (G, A, T, C). To each reaction mixture, we added these specific amounts of deoxynucleotides, and dideoxynucleotides.

| | Reaction Mixtures (Nanograms of Nucleotides) | | | |
|---|---|---|---|---|
| | G | A | T | C |
| Deoxynucleotides | | | | |
| dGTP | 1022.9 | 1077.4 | 1102.9 | 1102.9 |
| dCTP | 1015.9 | 992.4 | 1015.9 | 942.9 |
| dTTP | 1048.6 | 1048.6 | 972.5 | 1048.6 |
| dATP | 985.5 | 985.5 | 985.5 | 985.5 |
| Dideoxynucleotides | | | | |
| dGTP | 123.0 | — | — | — |
| dCTP | — | 29.7 | — | — |
| dTTP | — | — | 466.0 | — |
| dATP | — | — | — | 113.0 |

Figure 19A:
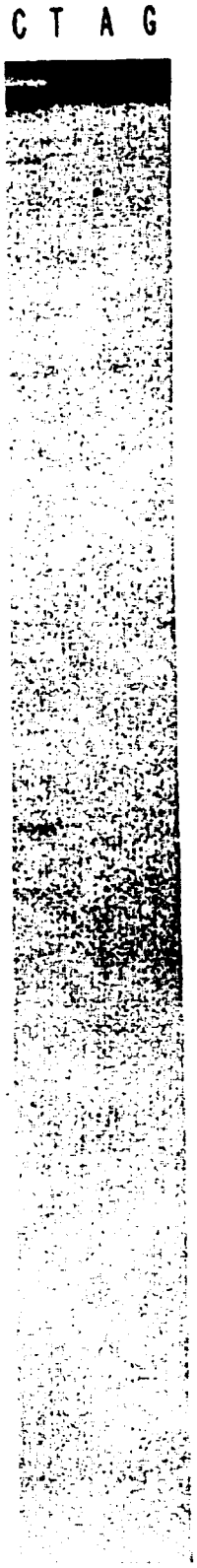
FIG. 19 shows a two-hour lumiautogram on X-ray film (A) and Polaroid instant black and white film (B) of DNA fragments visualized by AMPPD chemiluminescence following electrophoretic separation of DNA fragments produced by the Sanger sequencing protocol.
Figure 19B:
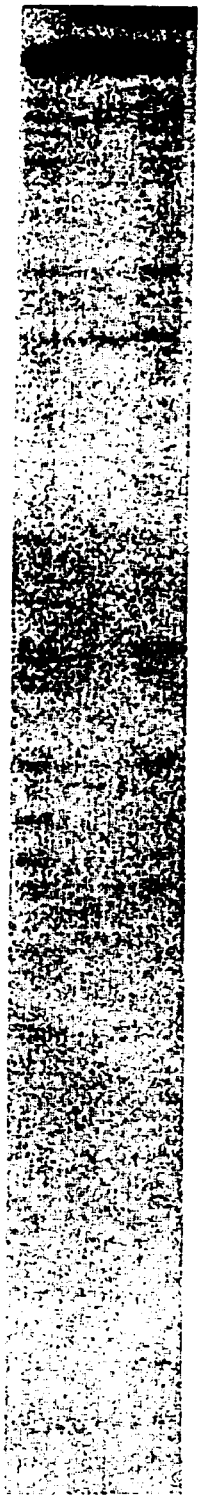

An aliquot of each reaction mixture (1 μl) was loaded on a standard sequencing gel and electrophoresed. The DNA was electrophoretically transferred to a Pall Biodyne A nylon membrane and then UV fixed to the membrane. The membrane was then dried, blocked for 1 hour with 0.2% casein in PBS (casein-PBS), incubated with streptavidin:alkaline phosphatase (1:5000 in casein-PBS) for 30 minutes, washed first with casein-PBS, then with 0.3% Tween 20 in PBS, and finally with 0.05 M bicarbonate/carbonate, pH 9.5, 1 mM $MgCl_2$. Substrate, 0.4 mM AMPPD in the final wash buffer, was incubated with the membrane for 5 minutes. After wrapping the membrane in plastic wrap, the membrane was placed in contact with Kodak XAR film and Polaroid Instant Black and White film for 2 hours. The order of sequence lanes is C T A G in FIGS. 19A (X-ray film) and 19B (instant film).

EXAMPLE 13

Effect of Membrane Composition on Detection of DNA Fragments by Chemiluminescence Various amounts of the SNAP® Hepatitis B core antigen oligonucleotide probe conjugated to alkaline phosphatase (Molecular Biosystems, Inc., San Diego, Calif.), as listed in the left column of Table VI, were spotted on three types of transfer membranes: Gene Screen Plus™ (Nylon), Schleicher and Schuell nitrocellulose, and Millipore PVDF. The spots were incubated with an AMPPD solution, luminescence generated, and light detected on instant film, as in Example 6(C).

The data of Table VI show the earliest detection times at each level of oligonucleotide for each of the three membranes. Luminescence was greatly increased in intensity by the use of nylon-based membranes, as compared to the other two types. For example, with a nylon membrane, the smallest amount of oligonucleotide tested, i.e., 0.01 ng, was detected within 60 seconds of film exposure. In contrast, it required at least 67 ng of oligonucleotide to be detectable in 60 seconds on a nitrocellulose membrane; amounts of 0.82 ng or less were not detectable within 10 minutes. In further contrast, no amount of oligonucleotide was detectable in periods as long as 10 minutes.

TABLE VI

| Oligonucleotide, | Earliest Detection Time, Sec. | | |
|---|---|---|---|
| ng | Nylon | Nitrocellulose | FVDF |
| 200 | 1 | 60 | * |
| 67 | 1 | 60 | * |
| 22 | 1 | 300 | * |
| 7.4 | 1 | 300 | * |
| 2.5 | 1 | 300 | * |
| 0.82 | 1 | * | * |
| 0.27 | 1 | * | * |
| 0.091 | 10 | * | * |
| 0.03 | 60 | * | * |
| 0.01 | 60 | * | * |

*Not detectable by 10 min. of exposure.

We claim:

[1. In an assay method in which a member of a specific binding pair is detected by means of an optically detectable reaction, the improvement wherein said optically detectable reaction includes the reaction, with, an enzyme, of a dioxetane having the formula

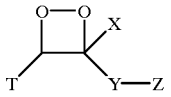

where T is a cycloalkyl or olycycloalkyl group bonded to the 4-membered ring portion of said dioxetane by a spiro linkage; Y is a fluorescent chromophore; X is hydrogen, alkyl, aryl, aralkyl, alkaryl, heteroalkyl, heteroaryl, cycloalkyl, cycloheteroalkyl, or enzyme-cleavable group; and Z is hydrogen or an enzyme-cleavable group, provided that at least one of X or Z must be an enzyme-cleavable group, so that said enzyme cleaves said enzyme-cleavable group from said dioxetane to form a negatively charged substituent bonded to said dioxetane, said negatively charged substituent causing said dioxetane to decompose to form a luminescent substance comprising said group Y of said dioxetane.]

[2. The method of claim 1 wherein said groups T, X, or Y, independently, further comprise a solubilizing substituent.]

[3. The method of claim 1 wherein said specific binding pair comprises an antigen and an antibody.]

[4. The method of claim 1 wherein said specific binding pair comprises a nucleic acid and a probe capable of binding to all or a portion of said nucleic acid.]

[5. The method of claim 1 wherein said group T of said dioxetane is a polycycloalkyl group.]

[6. The method of claim 1 wherein said group T is an adamantyl group.]

[7. The method of claim 1 wherein said enzyme cleavable group comprises phosphate, and said enzyme comprises phosphatase.]

[8. The method of claim 1 wherein said specific binding pair comprises an enzyme and a dioxetane containing a group cleavable by said enzyme.]

[9. The method of claim 1 wherein said enzyme-cleavable group comprises a galactopyranoside, and said enzyme comprises a galactosidase.]

[10. The method of claim 1 wherein said enzyme-cleavable group comprises a carboxylic acid ester, and said enzyme comprises an esterase.]

[11. The method of claim 1 further comprising, when applied to solid state methods, blocking nonspecific binding to solid matrices by pretreating said solid matrices with a poly(vinyl quaternary ammonium salt).]

[12. The method of claim 4 wherein the nucleic acid is DNA, RNA or fragment thereof.]

[13. The method of claim 4 wherein the probe is a labeled oligonucleotide complementary to the nucleic acid.]

[14. The method of claim 13 wherein the oligonucleotide probe is biotinylated.]

[15. The method of claim 12 wherein the DNA RNA or fragment thereof is produced by a sequencing protocol.]

16. [The method of claim 15] *In an assay method in which a member of a specific binding pair is detected by means of an optically detectable reaction, the improvement wherein said optically detectable reaction includes the reaction, with, an enzyme, of a dioxetane having the formula:*

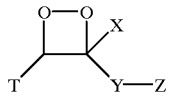

*where T is a cycloalkyl or olycycloalkyl group bonded to the 4-membered ring portion of said dioxetane by a spiro linkage; Y is a fluorescent chromophore; X is a hydrogen, alkyl, aryl, aralkyl, alkaryl, heteroalkyl, heteroaryl, cycloalkyl, cycloheteroalkyl, or enzyme cleavable group; and Z is hydrogen or an enzyme cleavable group, provided that at least one of X or Z must be an enzyme-cleavable group, so that said enzyme cleaves said enzyme-cleavable group from said dioxetane to form a negatively charged substituent bonded to said dioxetane, said negatively charged substituent causing said dioxetane to decompose to form a luminescent substance comprising said group Y of said dioxetane, wherein said specific binding pair comprises a nucleic acid which is DNA, RNA or a fragment thereof, produced by a sequencing protocol and a probe capable of binding to all or a portion of said nucleic acid,* further comprising the steps of (a) contacting the DNA, RNA or fragment thereof with a labeled complementary oligonucleotide probe to form a hybridizing pair, (b) contacting the hybridized pair with a molecule capable of strong binding to the label of the oligonucleotide covalently conjugated with an enzyme capable of cleaving [an enzyme-cleavable] *said* 1,2-dioxetane to release light energy, (c) adding [such a] *said* 1,2-dioxetane substrate, and (d) detecting the light produced.

17. The method of claim 16 wherein the oligonucleotide label is biotin or a biotin derivative.

18. The method of claim 16 wherein the molecule capable of strong interaction with the label of the oligonucleotide is avidin or streptavidin.

19. The method of claim 16 wherein the enzyme is a phosphatase and the 1,2-dioxetane is AMPPD.

20. The method of claim 16 wherein the enzyme is a galactosidase and the 1,2-dioxetane is AMPGD.

21. The method of claim 16 wherein light is detected by light-sensitive film.

22. The method of claim 16 wherein light is detected by a photoelectric cell.

23. The method of claim [13] *16*, wherein said oligonucleotide probe is covalently labeled with an enzyme capable of decomposing said 1,2-dioxetane to emit light.

24. The method of claim [13] *16*, wherein said label on said oligonucleotide probe comprises a covalently bound antigen that is immunochemically bound to an antibody-enzyme conjugate, wherein said antibody is directed to said antigen and said enzyme is capable of decomposing said 1,2-dioxetane to emit light.

25. The method of either claim 23 or 24, wherein said enzyme is an acid or alkaline phosphatase and said 1,2-dioxetane is AMPPD.

26. The method of [either claim 23 or 14] *claim 16*, wherein said enzyme is a galactosidase and said 1,2-dioxetane is AMPGD.

27. The method of either claim 23 or 24, wherein said enzyme is a carboxyl acid esterase and said 1,2-dioxetane is 3-(2'-spiroadamantane)-4-methoxy-4-(3"-acetoxy)phenyl-1,2-dioxetane.

28. The method of [any one of claims 4, 13 or 23–27, inclusive,] *claim 16*wherein the binding of said probe to said nuclei acid is carried out on a nylon membrane.

29. The method of claim 16, wherein said enzyme is a carboxylic acid esterase and said 1,2-dioxetane is 3-(2'-spiroadamantane)-4-methoxy-4-(3"-acetoxy)phenyl-1,2-dioxetane.

30. The method of any one of claims 16–20, inclusive, wherein the hybridizing between said DNA, RNA or fragment thereof and said labeled oligonucleotide probe is conducted on a nylon membrane.

[31. A kit for detecting a first substance in a sample comprising a dioxetane having the formula

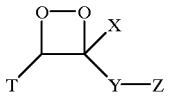

where T is a cycloalkyl group bonded to the 4-membered ring portion of said dioxetane by a spiro linkage; Y is a chromophore capable of fluorescence; X is hydrogen, alkyl, aryl, aralkyl, alkaryl, heteroalkyl, heteroaryl, cycloalkyl, cyclo heteroalkyl, or enzyme-cleavable group; and Z is hydrogen or an enzyme-cleavable group, provided that at least one of X or Z must be an enzyme-cleavable group; and an enzyme capable of cleaving said enzyme-cleavable group of said dioxetane.]

32. A kit for detecting a nucleic acid or fragment thereof in a sample by hybridization of said nucleic acid or fragment to a complementary labeled oligonucleotide probe, comprising a 1,2-dioxetane capable of producing light energy when decomposed having the formula

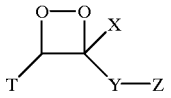

wherein T is a stabilizing cycloalkyl group spiro bonded to the 4-membered dioxetane ring, X is hydrogen, alkyl, aryl, aralkyl, alkaryl, heteroalkyl, heteroaryl, cycloalkyl, cyclo-heteroalkyl or an enzyme-cleavable group, Y is a chromophore capable of fluorescence, and Z is hydrogen or an enzyme-cleavable group provided that at least one of X or Z must be an enzyme-cleavable group; a covalently enzyme-labeled oligonucleotide probe; and, a nylon membrane upon which said nucleic acid-oligonucleotide probe hybridization is conducted.

33. The kit of claim 32, wherein said 1,2-dioxetane is AMPPD and said enzyme is acid or alkaline phosphatase.

34. The kit of claim 32, wherein said 1,2-dioxetane is AMPGD and said enzyme is galactosidase.

35. The kit of claim 32, wherein said enzyme is a carboxylic acid esterase and said 1,2-dioxetane is 3-(2'-spiroadamantane)-4-methoxy-4(3"-acetoxy)phenyl-1,2-dioxetane.

36. The kit of any one of claims [37–30] *32–35*, inclusive, further comprising image-reproducing means for detecting said light energy.

37. The kit of claim 36, wherein said image-producing means is photographic film.

38. A kit for detecting a nuclei acid or fragment thereof in a sample by hybridization of said nuclei acid or fragment to a complementary labeled oligonucleotide probe, comprising a 1,2-dioxetane capable of producing light energy when decomposed having the formula

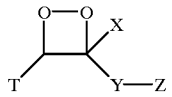

wherein T is a stabilizing cycloalkyl group spiro bonded to the 4-membered dioxetane ring, X is hydrogen, alkyl, aryl, aralkyl, alkaryl, heteroalkyl, heteroaryl, cycloalkyl, cyclo-heteroalkyl or an enzyme-cleavable group, Y is a chromophore capable of fluorescence, and Z is hydrogen or an enzyme-cleavable group, provided that at least one of X or Z must be an enzyme-cleavable group; a complementary oligonucleotide probe covalently labeled with biotin or a biotin derivative; avidin or streptavidin covalently bound to an enzyme capable of decomposing a 1,2-dioxetane to emit light; and, a nylon membrane upon which said nuclei acid or fragment thereof is hybridized to said oligonucleotide probe.

39. The kit of claim 38, wherein said 1,2-dioxetane is AMPPD and said enzyme is acid or alkaline phosphatase.

40. The kit of claim 38, wherein said 1,2-dioxetane is AMPGD and said enzyme is a galactosidase.

41. The kit of claim 38, wherein said 1,2-dioxetane is 3-(2'-spiroadamantane)-4-methoxy-4-(3"-acetoxy)phenyl-1,2-dioxetane and said enzyme is a carboxylic acid esterase.

42. The kit of any one of claims 38–41, inclusive, further comprising image-reproducing means for detecting said light energy.

43. The kit of claim 42, wherein said image-reproducing means is photographic film.

44. A kit for detecting a nucleic acid or fragment thereof in a sample by hybridization of said nuclei acid or fragment to a complementary labeled oligonucleotide probe, comprising a 1,2-dioxetane capable of producing light energy when decomposed having the formula

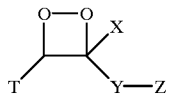

wherein T is a stabilizing cycloalkyl group spiro bonded to the 4-membered dioxetane ring, X is hydrogen, alkyl, aryl, aralkyl, alkaryl, heteroalkyl, heteroaryl, cycloalkyl, cyclo-heteroalkyl or an enzyme-cleavable group, Y is a chromophore capable of fluorescence, and Z is hydrogen or an enzyme-cleavable group, provided that at least one of X or Z must be an enzyme-cleavable group; a complementary oligonucleotide probe covalently labeled with an antigen; an antibody directed to said antigen covalently bound to an enzyme capable of decomposing a 1,2-dioxetane to emit light; and, a nylon membrane upon which said nucleic acid or fragment thereof is hybridized to said oligonucleotide probe.

45. The kit of claim 44, wherein said enzyme is an acid or alkaline phosphatase and said 1,2-dioxetane is AMPPD.

46. The kit of claim 44, wherein said enzyme is a galactosidase and said 1,2-dioxetane is AMPGD.

47. The kit of claim 44, wherein said enzyme is a carboxyl acid esterase and said 1,2-dioxetane is 3-(2'-spirodamantane)-4-methoxy-4-(3"-acetoxy)phenyl-1,2-dioxetane.

48. The kit of any one of the claims 44–47, inclusive, further comprising image-reproducing means for detecting said light energy.

49. The kit of claim 48, wherein said image-reproducing means is photographic film.

50. A kit for detecting a protein in a sample, comprising a 1,2-dioxetane capable of producing light energy when decomposed having the formula

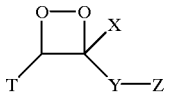

wherein T is a stabilizing cycloalkyl group spiro bonded to the 4-membered dioxetane ring, X is hydrogen, alkyl, aryl, aralkyl, alkaryl, heteroalkyl, heteroaryl, cycloalkyl, cycloheteroalkyl or an enzyme-cleavable group, Y is a chromophore capable of fluorescence, and Z is hydrogen or an enzyme-cleavable group, provided that at least one of X or Z must be an enzyme-cleavable group; an antibody directed to said protein covalently bound to an enzyme capable of decomposing said 1,2-dioxetane derivatives to emit light; and, a membrane upon which protein-antibody binding is conducted.

51. The kit of claim 50, wherein said membrane is a nylon or nitrocellulose membrane.

52. The kit of claim 50, wherein said 1,2-dioxetane is AMPPD and said enzyme is acid or alkaline phosphatase.

53. The kit of claim 50, wherein said 1,2-dioxetane is AMPGD and said enzyme is a galactosidase.

54. The kit of claim 50, wherein said 1,2-dioxetane is 3-(2'-spiroadamantane)-4-methoxy-4-(3"-acetoxy)phenyl-1,2-dioxetane and said enzyme is a carboxylic acid esterase.

55. The kit of any one of claims 50–54, inclusive, further comprising image-reproducing means for detecting said light energy.

56. The kit of claim 55, wherein said image reproducing means is photographic film.

57. A kit for detecting a protein in a sample comprising a 1,2-dioxetane capable of producing light energy when decomposed having the formula

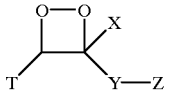

wherein T is a stabilizing cycloalkyl group spiro bonded to the 4-membered dioxetane ring, X is hydrogen, alkyl, aryl, aralkyl, alkaryl, heteroalkyl, heteroaryl, cycloalkyl, cycloheteroalkyl or an enzyme-cleavable group, Y is a chromophore capable of fluorescence, and Z is hydrogen or an enzyme-cleavable group, provided at at least one of X or Z must be an enzyme-cleavable group; a first antibody directed to said protein; and, a second antibody directed to said first antibody covalently bound to an enzyme capable of decomposing said 1,2-dioxetane derivative.

58. The kit of claim 57, wherein said 1,2-dioxetane is AMPPD and said enzyme is acid or alkaline phosphatase.

59. The kit of claim 57, wherein said 1,2-dioxetane is AMPGD and said enzyme is a galactosidase.

60. The kit of claim 57, wherein said 1,2-dioxetane is 3-(2'-spiroadamantane)-4-methoxy-4-(3"-acetoxy)phenyl-1,2-dioxetane and said enzyme is a carboxylic acid esterase.

61. The kit of [any one of claims 37, 43, 55 or 57,] *claim 32* further comprising a water-soluble enhancing substance that increases specific light energy production above that produced in its absence.

62. The kit of claim 61, wherein said water-soluble enhancing substance is serum albumin.

63. The kit of claim 61, wherein said enhancing substance is a polymeric quaternary ammonium salt.

64. The kit of claim 63 wherein said polymeric quaternary ammonium salt is poly(vinylbenzyltrimethylammonium chloride) or poly[vinylbenzyl(benzyldimethylammonium chloride)].

65. The kit of claim 61, wherein said enhancing substance comprises a positively charged polymeric quaternary ammonium salt and fluorescein capable of forming a ternary complex with the 1,2-dioxetane anion produced following enzyme-catalyzed decomposition of said 1,2-dioxetane, whereby energy transfer occurs between said 1,2-dioxetane anion and fluorescein and light is emitted by fluorescein.

66. The kit of claim 65 wherein said polymeric quaternary ammonium salt is poly(vinylbenzyltrimethylammonium chloride) or poly[vinylbenzyl(benzyldimethylammonium chloride)].

*67. In an assay method in which a member of a specific binding pair is detected by means of an optically detectable reaction, the improvement wherein said optically detectable reaction includes the reaction, with, an enzyme, of a dioxetane having the formula*

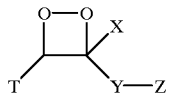

*where T is a cycloalkyl or polycycloalkyl group bonded to the 4-membered ring portion of said dioxetane by a spiro linkage; Y is a fluorescent chromophore; X is hydrogen, alkyl, aryl, aralkyl, alkaryl, heteroalkyl, heteraryl, cycloalkyl, cycloheteroalkyl, or enzyme-cleavable group; and Z is a hydrogen or an enzyme-cleavable group, provided that at least one of X or Z must be an enzyme-cleavable group, so that said enzyme cleaves said enzyme-cleavable group from said dioxetane to form a negatively charged substituent bonded to said dioxetane, said negatively charged substituent causing said dioxetane to decompose to form a luminescent substance comprising said group Y of said dioxetane, said reaction being conducted in the presence of a water-soluble enhancing substance that increases specific light energy production above that produced by decomposition of said dioxetane in the absence of said water-soluble enhancing substance.*

*68. The method of claim 67, wherein said groups T, X, or Y, independently, further comprises a solubilizing substituent.*

69. The method of claim 67, wherein said specific binding pair comprises an antigen and an antibody.

70. The method of claim 67, wherein said specific bind pair comprises an nucleic acid and a probe capable of binding to all or a portion of said nucleic acid.

71. The method of claim 67, wherein said group T is an adamantyl group.

72. The method of claim 71, wherein said enzyme cleavable group comprise phosphate, and said enzyme comprises phosphatase.

73. The method of claim 67, further comprising, when applied to solid state methods, blocking nonspecific binding to solid matrices by pretreating said solid matrices with a poly(vinyl quaternary ammonium salt).

74. The method of claim 70, wherein the nucleic acid is DNA, RNA or fragment thereof.

75. The method of claim 70, wherein the probe is a labeled oligonucleotide complementary to the nucleic acid.

76. The method of claim 75, wherein the oligonucleotide probe is biotinylated.

77. The method of claim 67, wherein said water-soluble enhancing substance is selected from the group consisting of serum albumin, poly(vinylbenzyltrimethylammonium chloride), poly(vinylbenzyl (benzyldimethylammoniumchloride)), and mixtures thereof, or said water-soluble enhancing substance comprises a positively charged polymeric quaternary ammonium salt and fluorescein which forms a ternary complex with the 1,2-dioxetane anion produced following enzyme-catalyzed decomposition of said 1,2-dioxetane, whereby energy transfer occurs between said 1,2-dioxetane anion and fluorescein and light is emitted by fluorescein.

78. The method of claim 67, wherein said water-soluble enhancing substance is a polymeric quaternary ammonium salt.

79. The method of claim 78, wherein said T is spiroadamantyl, and Y is phenyl.

80. A kit for detecting a first substance in a sample comprising a dioxetane having the formula

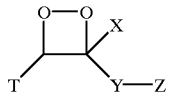

wherein T is a cycloalkyl group bonded to the 4-membered ring portion of said dioxetane by a spiro linkage; Y is a chromophore capable of fluorescence; X is hydrogen, alkyl, aryl, aralkyl, alkaryl, heteroalkyl, heteroaryl, cycloalkyl, cyclo heteroalkyl, or enzyme-cleavable group; and Z is hydrogen or an enzyme-cleavable group, provided that at least one of X or Z must be an enzyme-cleavable group; a water-soluble enhancing substance that increases specific light energy production above that produced by decomposition of said dioxetane in the absence of said water-soluble enhancing substance; and an enzyme capable of cleaving said enzyme-cleavable group of said dioxetane.

81. The kit of claim 80, wherein said kit further comprises a membrane.

82. The kit of claim 80, wherein said water-soluble enhancing substance is selected from the group consisting of serum albumin, poly(vinylbenzyltrimethylammonium chloride), poly[vinylbenzyl (benzyldimethylammoniumchloride)], and mixtures thereof, or said water-soluble enhancing substance comprises a positively charged polymeric quaternary ammonium salt and fluorescein which forms a ternary complex with the 1,2-dioxetane anion produced following enzyme-catalyzed decomposition of said 1,2-dioxetane, whereby energy transfer occurs between said 1,2-dioxetane anion and fluorescein and light is emitted by fluorescein.

83. The kit of claim 80, wherein said water-soluble enhancing substance is a polymeric quaternary ammonium salt.

84. The kit of claim 50, further comprising a secured antibody which binds to a complex comprising said further antibody bound to a protein.

85. A kit for detecting a protein in a sample, comprising a 1,2-dioxetane capable of producing light energy when decomposed having the formula

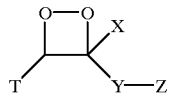

wherein T is a stabilizing cycloalkyl group spiro bonded to the 4-membered dioxetane ring, X is hydrogen, alkyl, aryl, aralkyl, alkaryl, heteroalkyl, heteroaryl, cycloalkyl, cycloheteroalkyl or an enzyme-cleavable group, Y is a chromophore capable of fluorescence, and Z id hydrogen or an enzyme-cleavable group, provided that at least one of X or Z must be an enzyme-cleavable group; an antibody directed to said protein; and water-soluble enhancing substance that increases specific light energy production upon decomposition of said dioxetane above that produced in its absence.

86. The kit of claim 85, wherein said water-soluble enhancing substance is a polymeric quaternary ammonium salt.

* * * * *